(12) United States Patent
Mortensen et al.

(10) Patent No.: US 12,214,327 B2
(45) Date of Patent: *Feb. 4, 2025

(54) ENDOTHERMIC REACTIONS HEATED BY RESISTANCE HEATING

(71) Applicant: HALDOR TOPSØE A/S, Kgs. Lyngby (DK)

(72) Inventors: Peter Mølgaard Mortensen, Roskilde (DK); Robert Klein, Roskilde (DK); Kim Aasberg-Petersen, Allerød (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 927 days.

This patent is subject to a terminal disclaimer.

(21) Appl. No.: 17/054,572

(22) PCT Filed: May 15, 2019

(86) PCT No.: PCT/EP2019/062424
§ 371 (c)(1),
(2) Date: Nov. 11, 2020

(87) PCT Pub. No.: WO2019/228798
PCT Pub. Date: Dec. 5, 2019

(65) Prior Publication Data
US 2021/0113983 A1 Apr. 22, 2021

(30) Foreign Application Priority Data
May 31, 2018 (DK) .......................... PA 2018 00249

(51) Int. Cl.
*B01J 12/00* (2006.01)
*B01J 19/00* (2006.01)
(Continued)

(52) U.S. Cl.
CPC ......... *B01J 12/007* (2013.01); *B01J 19/0013* (2013.01); *B01J 19/2485* (2013.01);
(Continued)

(58) Field of Classification Search
None
See application file for complete search history.

(56) References Cited

U.S. PATENT DOCUMENTS 3,499,947 A   3/1970   Johnson
4,157,356 A   6/1979   Bulford et al.
(Continued)

FOREIGN PATENT DOCUMENTS

CA   2427464 A1   4/1999
CN   1483133 A    3/2004
(Continued)

OTHER PUBLICATIONS

Danish Search Report issued in corresponding Patent Application No. PA 2019 01324 dated May 27, 2020, 8 pages.
(Continued)

*Primary Examiner* — Colin W. Slifka
(74) *Attorney, Agent, or Firm* — Boone IP Law

(57) ABSTRACT

A reactor system for carrying out an endothermic reaction of a feed gas, including: a structured catalyst arranged for catalyzing the endothermic reaction of a feed gas, the structured catalyst including a macroscopic structure of electrically conductive material, the macroscopic structure supporting a ceramic coating, wherein the ceramic coating supports a catalytically active material; a pressure shell housing the structured catalyst; heat insulation layer between the structured catalyst and the pressure shell; at least two conductors electrically connected to the electrically conductive material and to an electrical power supply placed outside the pressure shell, wherein the electrical (Continued)

power supply is dimensioned to heat at least part of said structured catalyst to a temperature of at least 200° C. by passing an electrical current through the electrically conductive material. Also, a process for performing an endothermic reaction of a feed gas.

18 Claims, 11 Drawing Sheets

(51) Int. Cl.
    *B01J 19/24*     (2006.01)
    *C01B 3/04*     (2006.01)
    *C01B 3/38*     (2006.01)
    *C01C 3/02*     (2006.01)
    *C07C 5/327*     (2006.01)
    *C07C 5/393*     (2006.01)

(52) U.S. Cl.
    CPC .............. *C01B 3/047* (2013.01); *C01B 3/384* (2013.01); *C01C 3/0208* (2013.01); *C07C 5/327* (2013.01); *C07C 5/393* (2013.01); *B01J 2219/0004* (2013.01); *B01J 2219/00135* (2013.01); *B01J 2219/00155* (2013.01); *C01B 2203/0233* (2013.01); *C01B 2203/085* (2013.01); *C01B 2203/1023* (2013.01); *C01B 2203/1235* (2013.01)

(56) References Cited

U.S. PATENT DOCUMENTS

| | | | |
|---|---|---|---|
| 4,520,224 | A | 5/1985 | Kamimura |
| 5,631,302 | A | 5/1997 | Koenig et al. |
| 5,827,901 | A | 10/1998 | Koenig et al. |
| 5,976,723 | A | 11/1999 | Boffito et al. |
| 6,322,757 | B1 | 11/2001 | Cohn et al. |
| 6,433,029 | B1 | 8/2002 | Fitzpatrick |
| 6,746,650 | B1 | 6/2004 | Lesieur |
| 7,960,441 | B2 | 6/2011 | Wolf |
| 8,568,581 | B2 | 10/2013 | Sivasankar et al. |
| 9,067,847 | B2 | 6/2015 | Bashir et al. |
| 11,214,488 | B2 | 1/2022 | Rueger |
| 2002/0051741 | A1 | 5/2002 | Abe et al. |
| 2002/0081253 | A1 | 6/2002 | Abe |
| 2002/0094312 | A1 | 7/2002 | Hanus et al. |
| 2002/0119084 | A1 | 8/2002 | Boneberg |
| 2004/0016650 | A1 | 1/2004 | Klug |
| 2004/0081875 | A1 | 4/2004 | Milliken et al. |
| 2004/0197246 | A1 | 10/2004 | Stevens et al. |
| 2004/0265225 | A1 | 12/2004 | Watson et al. |
| 2006/0116543 | A1 | 6/2006 | Bellet et al. |
| 2006/0124445 | A1 | 6/2006 | Labrecque et al. |
| 2006/0254141 | A1 | 11/2006 | Krause et al. |
| 2007/0045125 | A1 | 3/2007 | Hartvigsen et al. |
| 2008/0023338 | A1 | 1/2008 | Stoots et al. |
| 2008/0169449 | A1 | 7/2008 | Mundschau |
| 2009/0220390 | A1 | 9/2009 | Grouset |
| 2009/0235587 | A1 | 9/2009 | Hawkes et al. |
| 2009/0289227 | A1 | 11/2009 | Rising |
| 2009/0307975 | A1 | 12/2009 | Wolf |
| 2010/0111781 | A1 | 5/2010 | Takahashi et al. |
| 2010/0296984 | A1 | 11/2010 | Ando et al. |
| 2011/0020207 | A1 | 1/2011 | Siegert |
| 2011/0136027 | A1 | 6/2011 | Chen et al. |
| 2011/0253550 | A1 | 10/2011 | Hoffmann |
| 2011/0253551 | A1 | 10/2011 | Lane et al. |
| 2011/0293510 | A1 | 12/2011 | Grannell et al. |
| 2012/0228150 | A1 | 9/2012 | Kang et al. |
| 2012/0288776 | A1 | 11/2012 | Nagaosa |
| 2012/0326090 | A1 | 12/2012 | Han et al. |
| 2013/0345326 | A1 | 12/2013 | Bashir et al. |
| 2014/0272734 | A1 | 9/2014 | Braun et al. |
| 2014/0291162 | A1 | 10/2014 | Sala et al. |
| 2015/0129805 | A1 | 5/2015 | Karpenko et al. |
| 2015/0175509 | A1 | 6/2015 | Almqvist et al. |
| 2015/0299871 | A1 | 10/2015 | Chen et al. |
| 2016/0002036 | A1 | 1/2016 | Kolaczkowski et al. |
| 2016/0355932 | A1 | 12/2016 | Reytier et al. |
| 2017/0106360 | A1 | 4/2017 | Meriam |
| 2018/0066371 | A1 | 3/2018 | Hong et al. |
| 2018/0127668 | A1 | 5/2018 | Masel |
| 2018/0194632 | A1 | 7/2018 | Jakobsson et al. |
| 2019/0085250 | A1 | 3/2019 | Anzelmo et al. |
| 2019/0112187 | A1 | 4/2019 | Østberg et al. |
| 2019/0144376 | A1 | 5/2019 | Højlund Nielsen et al. |
| 2020/0095124 | A1 | 3/2020 | Rueger |
| 2020/0354216 | A1 | 11/2020 | Mortensen |
| 2021/0171344 | A1 | 6/2021 | Mortensen et al. |
| 2021/0238035 | A1 | 8/2021 | Mortensen et al. |
| 2022/0081289 | A1 | 3/2022 | De Sarkar et al. |

FOREIGN PATENT DOCUMENTS

| | | |
|---|---|---|
| CN | 101177239 A | 5/2008 |
| CN | 105188903 A | 12/2015 |
| DE | 102005046746 A1 | 4/2007 |
| DE | 102013102969 A1 | 9/2014 |
| DE | 102013226126 A1 | 6/2015 |
| EP | 0025205 A1 | 3/1981 |
| EP | 2491998 A1 | 8/2012 |
| EP | 2955158 A1 | 12/2015 |
| EP | 3249027 A1 | 11/2017 |
| EP | 2874738 B1 | 9/2018 |
| EP | 3415661 A1 | 12/2018 |
| EP | 3472370 A1 | 4/2019 |
| EP | 3574991 A1 | 12/2019 |
| GB | 722025 | 1/1955 |
| GB | 0915444 A | 1/1963 |
| GB | 1269311 A | 4/1972 |
| GB | 1338352 A | 11/1973 |
| GB | 2358148 A | 7/2001 |
| JP | H5-6120 U | 1/1993 |
| JP | 2008001584 A | 1/2008 |
| JP | 2014-152219 A | 8/2014 |
| KR | 10-2009-0068427 A | 6/2009 |
| KR | 10-2018-0075285 A | 7/2018 |
| WO | 0076651 A1 | 12/2000 |
| WO | 2004091773 A1 | 10/2004 |
| WO | 2007048641 A2 | 5/2007 |
| WO | 2007088923 A1 | 8/2007 |
| WO | 2010/004300 A1 | 1/2010 |
| WO | 2012084609 A1 | 6/2012 |
| WO | 2013/131778 A2 | 9/2013 |
| WO | 2014099567 A1 | 6/2014 |
| WO | 2014/154253 A1 | 10/2014 |
| WO | 2014/180888 A1 | 11/2014 |
| WO | 2015/014527 A1 | 2/2015 |
| WO | 2016/091636 A1 | 6/2016 |
| WO | 2017/014635 A1 | 1/2017 |
| WO | 2017036794 A1 | 3/2017 |
| WO | 2017186612 A1 | 11/2017 |
| WO | 2017186615 A1 | 11/2017 |
| WO | 2018/206235 A1 | 11/2018 |
| WO | 2018/228723 A1 | 12/2018 |
| WO | 2019/110266 A1 | 6/2019 |
| WO | 2019/110267 A1 | 6/2019 |
| WO | 2019104375 A1 | 6/2019 |
| WO | 2019110268 A1 | 6/2019 |
| WO | 2019/228796 A1 | 12/2019 |
| WO | 2019/228797 A1 | 12/2019 |
| WO | 2019228798 A1 | 12/2019 |
| WO | 2020/008008 A1 | 1/2020 |
| WO | 2020/035574 A1 | 2/2020 |
| WO | 2020/208008 A1 | 10/2020 |

OTHER PUBLICATIONS

International Search Report (PCT/ISA/210) and Written Opinion (PCT/ISA/237) mailed on Feb. 23, 2021, by the European Patent Office as the International Searching Authority for International Application No. PCT/EP2020/081700. (20 Pages).

(56) References Cited

OTHER PUBLICATIONS

Keim, W., "Synthesis Gas Feedstock for Chemicals", American Chemical Society, Jan. 1, 1987, vol. 25, No. 10, pp. 1-16. (16 pages).
Kongas, Rainer, "Review-Electrochemical CO2 Reduction for CO Production: Comparison of Low- and High-Temperature Electrolysis Technologies", Journal of the Electrochemical Society, Feb. 14, 2020, 167:0044508. (12 pages).
Wang, Y., et al., "High temperature solid oxide H2O/Co2 co-electrolysis for syngas production", Fuel Processing Technology, Nov. 14, 2016, vol. 161, pp. 248-258. (12 pages).
U.S. Appl. No. 17/046,475, filed Oct. 9, 2020, Peter Mølgaard Mortensen, filed Oct. 9, 2020, (Cited herein as U.S. Pat. No. 2021/0171344 of Jun. 10, 2021).
U.S. Appl. No. 17/636,945, filed Feb. 21, 2022, Peter Mølgaard Mortensen, filed Feb. 21, 2022.
U.S. Appl. No. 17/637,539, filed Feb. 23, 2022, Peter Mølgaard Mortensen, filed Feb. 23, 2022.
U.S. Appl. No. 17/638,423, filed Feb. 25, 2022, Peter Mølgaard Mortensen, filed Feb. 25, 2022.
U.S. Appl. No. 17/641,293, filed Mar. 8, 2022, Peter Mølgaard Mortensen, filed Mar. 8, 2022.
International Search Report (PCT/ISA/210) and Written Opinion (PCT/ISA/237) mailed on Jul. 26, 2019, by the European Patent Office as the International Searching Authority for International Application No. PCT/EP2019/062424.
Search Report mailed on Jan. 28, 2019, by the Danish Patent Office for Application No. PA 2018 00249.
Xu, "Methane steam reforming, methanation and water-gas shift: I. intrinsic kinetics", American Institution of Chemical Engineers Journal, vol. 35, No. 1, Jan. 1989, pp. 88-96.
U.S. Appl. No. 18/256,689, filed Jun. 13, 2023, Christian Wix.
U.S. Appl. No. 17/630,734, filed Jan. 27, 2022, Peter Mølgaard Mortensen.
U.S. Appl. No. 17/627,202, filed Jan. 14, 2022, Peter Mølgaard Mortensen.
Search Report dated Apr. 24, 2020, issued in the Danish Patent Application No. PA201901433, 9 pages.
Search Report dated Apr. 24, 2020, issued in the Danish Patent Application No. PA201901435, 9 pages.
International Search Report (PCT/ISA/210) and Written Opinion (PCT/ISA/237) dated Nov. 26, 2020, issued in the European patent Application No. PCT/EP2020/076704, 11 pages.
International Search Report (PCT/ISA/210) and Written Opinion (PCT/ISA/237) dated Nov. 26, 2020, issued in the European patent Application No. PCT/EP2020/076713, 10 pages.
Zhou et al., "Investigation of a Novel Porous Anodic Alumina Plate for Methane Steam Reforming: Hydrothermal Stability, Electrical Heating Possibility and Reforming Reactivity", International Journal of Hydrogen Energy, vol. 34, Issue 2, Jan. 2009, pp. 844-858.
Aasberg-Petersen, K., et al., "Synthesis gas production for FT synthesis," Studies in Surface Science and Catalysis, vol. 152, Chapter 4, 2004, p. 258-405, Elsevier B.V., The Netherlands.
Boccuzzi et al., "FTIR study of methanol decomposition on gold catalyst for fuel Cells", Journal of Power Sources, vol. 118, No. 1-2, May 25, 2003, pp. 304-310.
Danish Search Report dated Mar. 27, 2020 issued by the Danish Patent and Trademark Office in Danish Patent Application No. PA 201901437. (9 pages).
Danish Search Report for Danish Application No. PA 2019 01145 dated Mar. 12, 2020 (7 pages).
Danish Search Report for Danish Application No. PA 2019 01432 dated Mar. 27, 2020 (10 pages).
Danish Search Report issued in corresponding Patent Application No. PA 2019 01434 dated May 27, 2020 (8 pages).
European Search Report dated Jul. 11, 2018, by the European Patent Office for European Application No. 18175366.6 (7 pages).
International Preliminary Report on Patentability received for PCT Patent Application No. PCT/EP2019/062423, mailed on Dec. 10, 2020, 8 pages.
International Preliminary Report on Patentability received for PCT Patent Application No. PCT/EP2019/062424, mailed on Dec. 10, 2020, 8 pages.
International Search Report and Written Opinion received for PCT Patent Application No. PCT/EP2019/062423, mailed on Aug. 26, 2019, 10 pages.
International Search Report and Written Opinion received for PCT Patent Application No. PCT/EP2020/076695, mailed on Nov. 23, 2020, 11 pages.
International Search Report and Written Opinion received for PCT Patent Application No. PCT/EP2020/076698, mailed on Nov. 26, 2020, 9 pages.
International Search Report and Written Opinion received for PCT Patent Application No. PCT/EP2020/076700, mailed on Nov. 26, 2020, 11 pages.
International Search Report and Written Opinion received for PCT Patent Application No. PCT/EP2020/076707, mailed on Nov. 27, 2020, 11 pages.
Wismann, Sebastian T., et al., "Electrified methane reforming: A compact approach to greener industrial hydrogen production," Science, May 24, 2019, p. 756-759, vol. 364, American Association for the Advancement of Science, Washington, D.C.
Technology for Application of Industrial Control Computers, pp. 303-304, Beijing: Chemical Engineering Press, May 1982.
Introduction to Energy Chemistry, Dong Guanghua, etc., p. 124, Xuzhouo: China University of Mining and Technology Press, Sep. 2018.
Bonis, L.J. and H.H. Hausner, Fundamental Phenomena in the Material Sciences, vol. 1: Sintering and Plastic Deformation, pp. v-101, 1964 (Year: 1964).

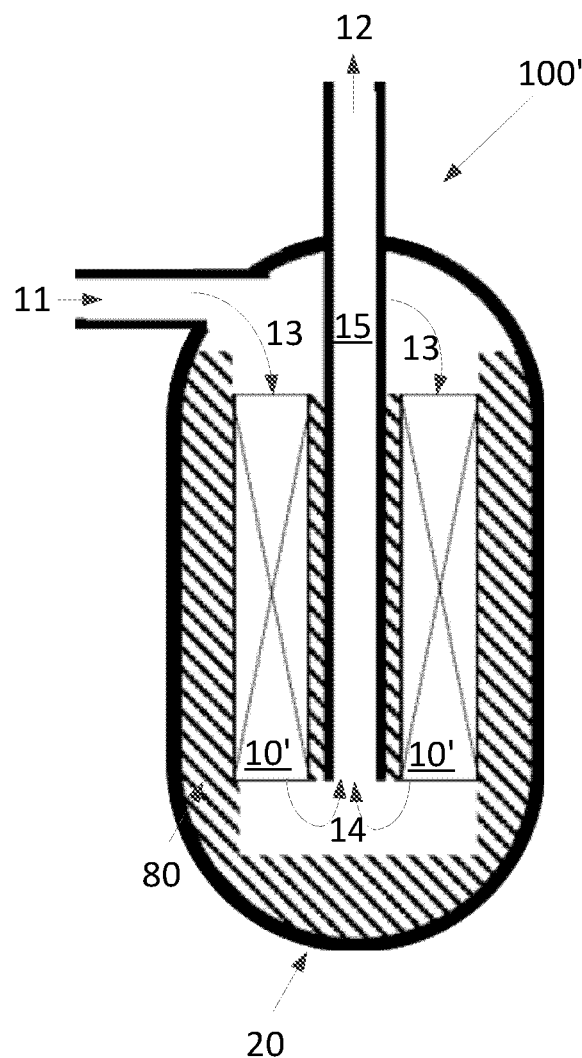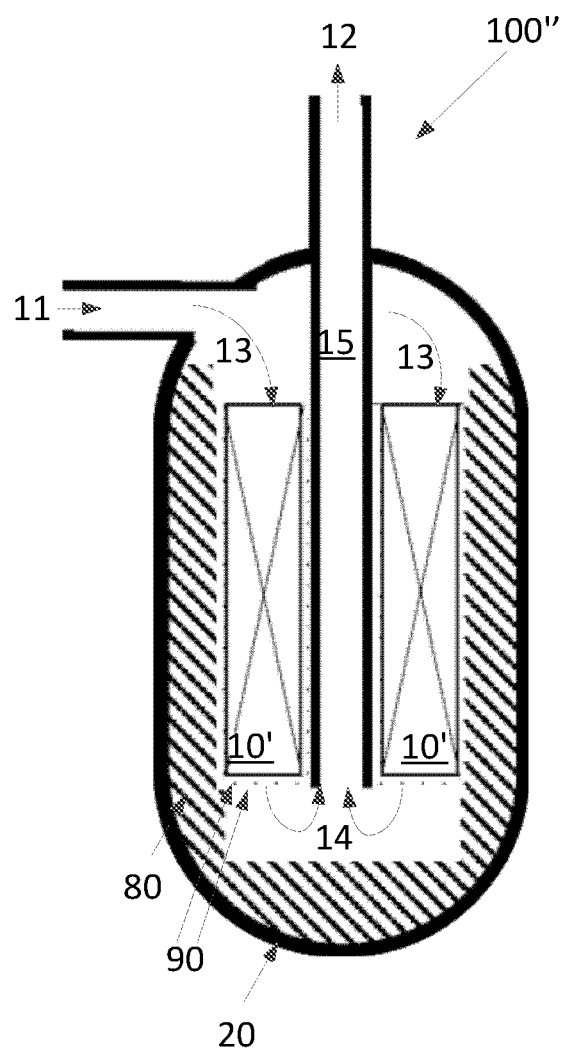
Fig. 3a                    Fig. 3b

ENDOTHERMIC REACTIONS HEATED BY RESISTANCE HEATING

FIELD OF THE INVENTION

Embodiments of the invention relate to a reactor system and a process for carrying out steam reforming of a feed gas comprising hydrocarbons where the heat for the endothermic reaction is provided by resistance heating.

BACKGROUND

Endothermic reactions will often be challenged by how efficient heat can be transferred to the reactive zone of the catalyst bed within a reactor unit. Conventional heat transfer by convection, conduction and/or radiation heating can be slow and will often meet large resistance in many configurations. This challenge can be illustrated with the tubular reformer in a steam reforming plant, which practically can be considered as a large heat exchanger with heat transfer as the rate limiting step. The temperature at the innermost part of the tubes of the tubular reformer is somewhat lower than the temperature outside the tubes due to the heat transfer rate through the walls of the tube and to the catalyst within the tubes as well as due to the endothermic nature of the steam reforming reaction.

One way to supply heat within catalyst instead of outside the reactor housing the catalyst is by means of electrical resistance heating. DE102013226126 describes a process for allothermal methane reforming with physical energy reclamation, wherein methane is reformed by means of carbon dioxide to synthesis gas consisting of carbon monoxide and hydrogen. The starting gases $CH_4$ and $CO_2$ are conducted in a fixed bed reactor consisting of electrically conductive and catalytic particles, which is electrically heated to temperatures of about 1000 K. The conversion of the reactant gases and the generation of heat of the generated synthesis gas take place in the fixed bed reactor.

It is an object of the invention to provide an alternative configuration of an electrically heated reactor system for carrying out steam reforming.

It is also an object of the invention to provide a reactor system with integrated heat supply and catalysts.

It is furthermore an object of the invention to provide a process for an endothermic reaction where the temperature of the endothermic reaction is controlled precisely to limit unwanted side reaction, as e.g. cracking of hydrocarbons in the dehydrogenation reactions.

An advantage of the invention is that the overall emission of carbon dioxide and other emissions detrimental to the climate may be reduced considerably, in particular if the power used in the reactor system is from renewable energy resources.

SUMMARY OF THE INVENTION

Embodiments of the invention generally relate to a reactor system for carrying out an endothermic reaction of a feed gas, the reactor system comprising:
- a structured catalyst arranged for catalyzing the endothermic reaction of a feed gas, where the structured catalyst comprises a macroscopic structure of electrically conductive material, where the macroscopic structure supports a ceramic coating and
- wherein the ceramic coating supports a catalytically active material;
- a structured catalyst arranged for catalyzing said endothermic reaction of a feed gas, said structured catalyst comprising an electrically conductive material and a catalyst material;
- a pressure shell housing said structured catalyst;
- a heat insulation layer between said structured catalyst and said pressure shell;
- at least two conductors electrically connected to said structured catalyst and to an electrical power supply placed outside the pressure shell, wherein the electrical power supply is dimensioned to heat at least part of the structured catalyst to a temperature of at least 200° C. by passing an electrical current through the electrically conductive material.

The layout of the reactor system allows for feeding a pressurized feed gas to the reactor system at an inlet and directing this gas into the pressure shell of the reactor system. Inside the pressure shell, a configuration of heat insulation layers and inert material is arranged to direct the feed gas through the structured catalyst where it will be in contact with the catalyst material, where the catalytically active material will facilitate the steam reforming reaction. Additionally, the heating of the structured catalyst will supply the required heat for the endothermic reaction. The product gas from the heated structured catalyst is led to the reactor system outlet.

The close proximity between the catalytically active material and the electrically conductive materials enables efficient heating of the catalytically active material by close proximity heat conduction from the resistance heated electrically conductive material. An important feature of the resistance heating process is thus that the energy is supplied inside the object itself, instead of being supplied from an external heat source via heat conduction, convection and radiation. Moreover, the hottest part of the reactor system will be within the pressure shell of the reactor system. Preferably, the electrical power supply and the structured catalyst are dimensioned so that at least part of the structured catalyst reaches a temperature of 850-1100° C. when the endothermic reaction is the steam reforming reaction, a temperature of 700-1200° C. when the endothermic reaction is the hydrogen cyanide synthesis, a temperature of 500-700° C. when the endothermic reaction is dehydrogenation, a temperature of 200-300° C. when the endothermic reaction is the methanol cracking, and a temperature of ca. 500° C. when the endothermic reaction is the ammonia cracking reaction. The surface area of the electrically conductive material, the fraction of the electrically conductive material coated with a ceramic coating, the type and structure of the ceramic coating, and the amount and composition of the catalytically active catalyst material may be tailored to the specific endothermic reaction at the given operating conditions.

In an embodiment, the electrically conductive material is a macroscopic structure. As used herein, the term "macroscopic structure" is meant to denote a structure that is large enough to be visible with the naked eye, without magnifying devices. The dimensions of the macroscopic structure are typically in the range of centimeters or even meters. Dimensions of the macroscopic structure are advantageously made to correspond at least partly to the inner dimensions of the pressure shell housing the structured catalyst, saving room for the heat insulation layer and conductors. Two or more macroscopic structures may be connected in order to provide an array of macroscopic structures having at least one of the outer dimensions in the range of meters, such as 2 m or 5 m. Such two or more macroscopic structures may be denoted "an array of macroscopic structures". In this case the dimensions of an array of macroscopic structures are advantageously made to correspond at least partly to the inner dimension of the pressure shell housing the structured catalyst (saving room for the heat insulation layer). A conceivable array of macroscopic structures could take up a volume of 0.1 to 10 m³ or even larger. The structured catalyst may comprise a single macroscopic structure or an array of macroscopic structures, where the macroscopic structure(s) support(s) a ceramic coating supporting catalytically active material. In an array of macroscopic structures, the macroscopic structures may be electrically connected to each other; however, alternatively, the macroscopic structures are not electrically connected to each other. Thus, the structured catalyst may comprise two or more macroscopic structures positioned adjacent to each other. The macroscopic structure(s) may be extruded and sintered structures or 3D printed structures. A 3D printed macroscopic structure can be provided with or without subsequent sintering.

The physical dimensions of the macroscopic structure may be any appropriate dimensions; thus, the height may be smaller than the width of the macroscopic structure or vice versa.

The macroscopic structure supports a ceramic coating, where the ceramic coating supports a catalytically active material. The term "macroscopic structure supporting a ceramic coating" is meant to denote that the macroscopic structure is coated by the ceramic coating at, at least, a part of the surface of the macroscopic structure. Thus, the term does not imply that all the surface of the macroscopic structure is coated by the ceramic coating; in particular, at least the parts of the macroscopic structure which are electrically connected to the conductors do not have a coating thereon. The coating is a ceramic material with pores in the structure, which allows for supporting catalytically active material on and inside the coating. Advantageously, the catalytically active material comprises catalytically active particles having a size in the range from about 5 nm to about 250 nm.

Preferably, the macroscopic structure has been manufactured by extrusion of a mixture of powdered metallic particles and a binder to an extruded structure and subsequent sintering of the extruded structure, thereby providing a material with a high geometric surface area per volume. Preferably, the extruded structure is sintered in a reducing atmosphere to provide the macroscopic structure. Alternatively, the macroscopic structure is 3D printed a metal additive manufacturing melting process, viz. a 3D printing processes, which do not require subsequent sintering, such as powder bed fusion or direct energy deposition processes. Examples of such powder bed fusion or direct energy deposition processes are laser beam, electron beam or plasma 3D printing processes. As another alternative, the macroscopic structure may have been manufactured as a 3D metal structure by means of a binder-based metal additive manufacturing process, and subsequent sintered in a non-oxidizing atmosphere at a first temperature $T_1$, where $T_1 > 1000°$ C., in order to provide the macroscopic structure.

A ceramic coating, which may contain the catalytically active material, is provided onto the macroscopic structure before a second sintering in an oxidizing atmosphere, in order to form chemical bonds between the ceramic coating and the macroscopic structure. Alternatively, the catalytically active material may be impregnated onto the ceramic coating after the second sintering. When chemical bonds are formed between the ceramic coating and the macroscopic structure an especially high heat conductivity between the electrically heated macroscopic structure and the catalytically active material supported by the ceramic coating is possible, offering close and nearly direct contact between the heat source and the catalytically active material of the structured catalyst. Due to close proximity between the heat source and the catalytically active material the heat transfer is effective, so that the structured catalyst can be very efficiently heated. A compact reactor system in terms of gas processing per reactor system volume is thus possible, and therefore the reactor system housing the structured catalyst may be compact.

As used herein, the terms "3D print" and "3D printing" is meant to denote a metal additive manufacturing process. Such metal additive manufacturing processes cover 3D printing processes in which material is joined to a structure under computer control to create a three-dimensional object, where the structure is to be solidified, e.g. by sintering, to provide the macroscopic structure. Moreover, such metal additive manufacturing processes cover 3D printing processes, which do not require subsequent sintering, such as powder bed fusion or direct energy deposition processes. Examples of such powder bed fusion or direct energy deposition processes are laser beam, electron beam or plasma 3D printing processes.

The reactor system of the invention does not need a furnace and this reduces the overall reactor size considerably.

In an embodiment, the electrically conductive material is an embedded resistor embedded in the catalyst material of the structured catalyst. This embedded resistor can be in any appropriate form of plates, spirals, rods, or similar, where the catalyst material is positioned to surround, or in another way be in close contact to, the embedded resistor.

In an embodiment, the embedded resistor supports a ceramic coating, wherein the ceramic coating supports a catalytically active material. Thus, the embedded resistor may, similar to the macroscopic support, be coated with a ceramic coating to directly support a catalytically active phase while still being embedded in the catalyst material. In this embodiment, the catalyst material surrounds the embedded resistor and the structured catalyst comprises catalyst material in the form of catalyst pellets, extrudates or granulates. The catalyst material may comprise an appropriate combination of catalyst support and catalytically active phase to facilitate the endothermic reaction.

Preferably, the electrically conductive material comprises Fe, Cr, Al or an alloy thereof. Such an alloy may comprise further elements, such as Si, Mn, Y, Zr, C, Co or combinations thereof. Preferably, the catalytically active material is particles having a size from 5 nm to 250 nm. Preferably, the conductors and the electrically conductive material are made of different materials than the electrically conductive material. The conductors may for example be of iron, nickel, aluminum, copper, silver or an alloy thereof. The ceramic coating is an electrically insulating material and will typically have a thickness in the range of around 100 μm, say 10-500 μm.

The electrically conductive material is advantageously a coherent or consistently intra-connected material in order to achieve electrical conductivity throughout the electrically conductive material, and thereby achieve thermal conductivity throughout the structured catalyst and in particular providing heating of the catalyst material. By the coherent or consistently intra-connected material it is possible to ensure uniform distribution of current within the electrically conductive material and thus uniform distribution of heat within the structured catalyst. Throughout this text, the term "coherent" is meant to be synonymous to cohesive and thus refer to a material that is consistently intra-connected or consistently coupled. The effect of the structured catalyst being a coherent or consistently intra-connected material is that a control over the connectivity within the material of the structured catalyst and thus the conductivity of the electrically conductive material is obtained. It is to be noted that even if further modifications of the electrically conductive material are carried out, such as provision of slits within parts of the electrically conductive material or the implementation of insulating material within the electrically conductive material, the electrically conductive material is still denoted a coherent or consistently intra-connected material.

The gas flow over the structured catalyst may be axial or co-axial with the current path through the structured catalyst, perpendicular to the current path or have any other appropriate direction in relation to the current path.

In this context, the term feed gas is meant to denote a gas having a suitable composition for the given endothermic reaction. When the endothermic reaction is steam methane reforming this may be typically be hydrocarbons, methane, hydrogen, carbon monoxide, carbon dioxide, steam, and inerts as nitrogen and argon. When the endothermic reaction is dehydrogenation it may be a hydrocarbon as propane or styrene together with inert and potentially hydrogen. When the endothermic reaction is hydrogen cyanide synthesis or a synthesis process for organic nitriles it may be higher hydrocarbons, ammonia, methane, nitrogen, hydrogen, oxygen, and/or inert. When the endothermic reaction is methanol cracking it may be methanol, steam, carbon monoxide, carbon dioxide, hydrogen, and inert. When the endothermic reaction is ammonia cracking it may be ammonia, hydrogen, nitrogen, and inert.

Moreover, the term "steam reforming" is meant to denote a reforming reaction according to one or more of the following reactions:

$$CH_4 + H_2O \leftrightarrow CO + 3H_2 \qquad (i)$$

$$CH_4 + 2H_2O \leftrightarrow CO_2 + 4H_2 \qquad (ii)$$

$$CH_4 + CO_2 \leftrightarrow 2CO + 2H_2 \qquad (iii)$$

Reactions (i) and (ii) are steam methane reforming reactions, whilst reaction (iii) is the dry methane reforming reaction.

For higher hydrocarbons, viz. $C_nH_m$, where n≥2, m≥4, equation (i) is generalized as:

$$C_nH_m + n\,H_2O \leftrightarrow nCO + (n+m/2)H_2 \qquad (iv)$$

where n≥2, m≥4.

Typically, steam reforming is accompanied by the water gas shift reaction (v):

$$CO + H_2O \leftrightarrow CO_2 + H_2 \qquad (v)$$

The term "steam methane reforming" is meant to cover the reactions (i) and (ii), the term "steam reforming" is meant to cover the reactions (i), (ii) and (iv), whilst the term "methanation" covers the reverse reaction of reaction (i). In most cases, all of these reactions (i)-(v) are at, or close to, equilibrium at the outlet from the reactor system. The term "prereforming" is often used to cover the catalytic conversion of higher hydrocarbons according to reaction (iv). Prereforming is typically accompanied by steam reforming and/or methanation (depending upon the gas composition and operating conditions) and the water gas shift reaction. Prereforming is often carried out in adiabatic reactors but may also take place in heated reactors.

The term "hydrogen cyanide synthesis" is meant to denote the following reactions:

$$2CH_4 + 2NH_3 + 3O_2 \leftrightarrow 2HCN + 6H_2O \qquad (vi)$$

$$CH_4 + NH_3 \leftrightarrow HCN + 3H_2 \qquad (vii)$$

The term "dehydrogenation" is meant to denote the following reactions:

$$R_1-CH_2-CH_2-R_2 \leftrightarrow R_1-CH=CH-R_2 \qquad (viii)$$

Where $R_1$ and $R_2$ may be any appropriate group in a hydrocarbon molecule, such as —H, —$CH_3$, —$CH_2$, or —CH.

The term "methanol cracking" is meant to denote the following reactions:

$$CH_3OH \leftrightarrow CO + 2H_2 \qquad (ix)$$

$$CH_3OH + H_2O \leftrightarrow CO_2 + 3H_2 \qquad (x)$$

Typically, methanol cracking reaction is accompanied by the water gas shift reaction (v).

The term "ammonia cracking" is meant to denote the following reactions:

$$2NH_3 \leftrightarrow N_2 + 3H_2 \qquad (xi)$$

As example, the steam reforming reaction is highly endothermic. High temperatures typically in excess of 800-850° C. are needed to reach acceptable conversions of the methane in the feed. A SMR consists of a number of tubes filled with catalyst pellets placed inside a furnace. The tubes are typically 10-13 meters long and will typically have an inner diameter between 80 and 160 mm. Burners placed in the furnace provide the required heat for the reactions by combustion of a fuel gas. A maximum average heat flux of 80000-90000 kcal/h/m² of inner tube surface is not uncommon. There is a general limitation to the obtainable heat flux due to mechanical constraints and the capacity is therefore increased by increasing the number of tubes and the furnace size. More details on the SMR type reactor system can be found in the art, e.g. "Synthesis gas production for FT synthesis"; Chapter 4, p. 258-352, 2004.

The term "electrically conductive" is meant to denote materials with an electrical resistivity in the range from: $10^{-5}$ to $10^{-8}$ Ω·m at 20° C. Thus, materials that are electrically conductive are e.g. metals like copper, silver, aluminum, chromium, iron, nickel, or alloys of metals. Moreover, the term "electrically insulating" is meant to denote materials with an electrical resistivity above 10 Ω·m at 20° C., e.g. in the range from $10^9$ to $10^{25}$ Ω·m at 20° C.

When the reactor system comprises a heat insulation layer between the structured catalyst and the pressure shell, appropriate heat and electrical insulation between the structured catalyst and the pressure shell is obtained. The presence of heat insulating layer between the pressure shell and the structured catalyst assists in avoiding excessive heating of the pressure shell, and assists in reducing thermal losses to the surroundings. The temperatures of the structured catalyst may reach up to about 1300° C., at least at some parts thereof, but by using the heat insulation layer between the structured catalyst and the pressure shell the temperature of the pressure shell can be kept at significantly lower temperatures of say 500° C. or even 100° C., which is advantageous as typical construction steel materials typically are unsuitable for pressure bearing application at temperatures above 1000° C. Moreover, a heat insulating layer between the pressure shell and the structured catalyst assists in control of the electrical current within the reactor system, since heat insulation layer is also electrically insulating. The heat insulation layer could be one or more layers of solid material, such as ceramics, inert material, bricks or a gas barrier or a combination thereof. Thus, it is also conceivable that a purge gas or a confined gas constitutes or forms part of the heat insulation layer.

Moreover, it should be noted that the term "heat insulating material" is meant to denote materials having a thermal conductivity of about 10 $W \cdot m^{-1} \cdot K^{-1}$ or below. Examples of heat insulating materials are ceramics, bricks, alumina based materials, zirconia based materials and similar.

Advantageously, any relevant gaps between structured catalyst, the heat insulation layer, the pressure shell, and/or any other components inside the reactor system is filled with inert material, e.g. in the form of inert pellets. Such gaps are e.g. a gap between the lower side of the structured catalyst and the bottom of the pressure shell and a gap between the sides of the structured catalyst and the insulation layer covering the inner sides of the pressure shell. The inert material may e.g. be a ceramic material in the form of pellets or tiles. The inert material assists in controlling the gas distribution through the reactor system and in controlling the flow of the gas through the structured catalyst. Moreover, the inert material typically has a heat insulating effect.

In an embodiment, the pressure shell has a design pressure of between 2 bar and 30 bar. The actual operating pressure will be determined by the endothermic reaction, the size of the plants, among other aspects. As the hottest part of the reactor system is the electrically conductive material, which will be surrounded by heat insulation layer and within the pressure shell of the reactor system, the temperature of the pressure shell can be kept significantly lower than the maximum process temperature. This allows for having a relative low design temperature of the pressure shell of e.g. 700° C. or 500° C. or preferably 300° C. or 100° C. of the pressure shell whilst having maximum process temperatures of 400° C., or even 900, or even 1100° C., or even up to 1300° C. on the structured catalyst. Material strength is higher at the lower of these temperatures (corresponding to the design temperature of the pressure shell as indicated above). This offers advantages when designing the chemical reactor.

In an embodiment, the pressure shell has a design pressure of between 30 bar and 200 bar, preferably between 80 and 180 bar.

In an embodiment, the resistivity of the electrically conductive material is between $10^{-5}$ $\Omega \cdot m$ and $10^{-7}$ $\Omega \cdot m$. A material with a resistivity within this range provides for an efficient heating of the structured catalyst when energized with a power source. Graphite has a resistivity of about $10^{-5}$ $\Omega \cdot m$ at 20° C., kanthal has a resistivity of about $10^{-6}$ $\Omega \cdot m$ at 20° C., whilst stainless steel has a resistivity of about $10^{-7}$ $\Omega \cdot m$ at 20° C. The electrically conductive material may for example be made of FeCrAlloy having a resistivity of ca. $1.5 \cdot 10^{-6}$ $\Omega \cdot m$ at 20° C.

In an embodiment, the pressure shell comprises an inlet for letting in process gas and an outlet for letting out product gas, wherein the inlet is positioned close to a first end of the pressure shell and the outlet is positioned close to a second end of the pressure shell, and wherein the at least two conductors both are connected to the structured catalyst at a position on the structured catalyst closer to the inlet than to the outlet. Hereby, the at least two conductors can be placed in the substantially colder part of the reactor system as the inlet gas will have lower temperature than the product gas, the electrically conductive material will be colder in the colder in the most upstream part of the material due to the heat consumed by the progress of the chemical reaction, and the feed gas fed led through the inlet may cool the at least two conductors before being heated by the heated structured catalyst further along the path of the gas over the heated structured catalyst. It is an advantage that the temperature of all electrically conducting elements except the electrically conductive material is kept down in order to protect the connections between the conductors and the structured catalyst. When the temperature of the conductors and other electrically conducting elements, except the electrically conductive material, is relatively low, less limitations on materials suitable for the conductors and other electrically conducting elements, except the electrically conductive material, exists. When the temperature of the electrically conducting elements increase, the resistivity thereof increases; therefore, it is desirable to avoid unnecessary heating of all other parts than the electrically conductive materials within the reactor system. The term "electrically conducting elements, except the electrically conductive material" is meant to cover the relevant electrically conducting elements arranged to connect the power supply to the structured catalyst.

In another embodiment, the two conductors of the reactor system may be provided at different ends of the structured catalyst.

It should be noted, that the system of the invention may include any appropriate number of power supplies and any appropriate number of conductors connecting the power supply/supplies and the electrically conductive material(s) of the structured catalyst.

According to an embodiment of the reactor system, the at least two conductors are led through a pressure shell in a fitting so that the at least two conductors are electrically insulated from the pressure shell. The fitting may be, partly, of a plastic and/or ceramic material. The term "fitting" is meant to denote a device that allows for mechanically connecting two pieces of hardware in a pressure bearing configuration. Thereby, the pressure within the pressure shell may be maintained even though the at least two conductors are lead through it. Non-limiting examples of the fittings may be an electrically insulating fitting, a dielectric fitting, a power compression seal, a compression fitting or a flange. The pressure shell typically comprises side walls, end walls, flanges and possibly further parts. The term "pressure shell" is meant to cover any of these components.

In an embodiment, the pressure shell further comprises one or more inlets close to or in combination with at least one of the fittings in order to allow a cooling gas to flow over, around, close to or inside at least one conductor within said pressure shell. Hereby, the conductors are cooled and thus the temperature that the fitting experiences is kept down. If the cooling gas is not used, the conductors may be heated by the feed gas to the reactor system, resistance heating of conductor due to the applied current, and/or heat conduction from the structured catalyst. The cooling gas could e.g. be hydrogen, nitrogen, steam, carbon dioxide or mixtures thereof. The temperature of the cooling gas at entry into the pressure shell may be e.g. about 100° C. or 200° C. or 250° C. In an embodiment, the conductor(s) is (are) hollow so that the cooling gas may flow through the conductor(s) and cool it (them) from within. By keeping the temperature of the fitting low, e.g. at around 100-200° C., it is easier to have a leak tight configuration. In an embodiment, a part of the feed gas, such as one of the reactants, is fed to the pressure shell as the cooling gas. In another embodiment, part of the feed gas or a gas with the same composition as the feed gas is used as cooling gas.

In an embodiment, the reactor system further comprises an inner tube in heat exchange relationship with the structured catalyst, where the inner tube is adapted to withdraw a product gas from the structured catalyst so that the product gas flowing through the inner tube or tubes is in heat exchange relationship with the gas flowing over the structured catalyst, but electrically separated from the structured catalyst. This is a layout which here is denoted a bayonet reactor system. In this layout the product gas within the inner tube assists in heating the process gas flowing over the structured catalyst. The electrical insulation between the inner tube and the structured catalyst could be gas in the form of a gap or distance between the inner tube and the structured catalyst or inert material loaded around the inner tube and the structured catalyst. The gas may pass through the structured catalyst in an up-flow or a downflow direction.

In an embodiment, the connection between the structured catalyst and the at least two conductors is a mechanical connection, a welded connection, a brazed connection or a combination thereof. The structured catalyst may comprise terminals physically and electrically connected to the structured catalyst in order to facilitate the electrical connection between the electrically conductive material and the at least two conductors. The term "mechanical connection" is meant to denote a connection where two components are held together mechanically, such as by a threaded connection or by clamping, so that a current may run between the components.

In an embodiment, the electrically conductive materials placed in an array of electrically conductive materials may be electrically connected to each other. The connection between the two or more electrically conductive materials may be by mechanical connection, clamping, soldering, welding or any combination of these connection methods. Each electrically conductive material may comprise terminals in order to facilitate the electrical connections. The two or more electrically conductive materials may be connected to the power supply in serial or parallel connection. The electrical connection between the two or more electrically conductive materials is advantageously coherent and uniform along the connection surface between the two or more electrically conductive materials, so that the two or more electrically conductive materials act as a single coherent or consistently intra-connected material; hereby, uniform electrical conductivity throughout the two or more electrically conductive materials is facilitated. Alternatively, or additionally, the structured catalyst may comprise an array of electrically conductive materials that are not electrically connected to each other. Instead, two or more electrically conductive materials are placed together within the pressure shell, but not connected electrically to each other. In this case, the structured catalyst thus comprises electrically conductive materials connected in parallel to the power supply.

A ceramic coating, with or without catalytically active material, may be added directly to a metal surface of the electrically conductive material by wash coating. The wash coating of a metal surface is a well-known process; a description is given in e.g. Cybulski, A., and Moulijn, J. A., "Structured catalysts and reactors", Marcel Dekker, Inc, New York, 1998, Chapter 3, and references herein. The ceramic coat may be added to the surface of the electrically conductive material and subsequently the catalytically active material may be added; alternatively, the ceramic coat comprising the catalytically active material is added to the macroscopic structure or electrically conductive material. The ceramic coating may for example be an oxide comprising Al, Zr, Mg, Ce and/or Ca. Exemplary coatings are calcium aluminate or a magnesium aluminum spinel. Such a ceramic coating may comprise further elements, such as La, Y, $T_1$, K or combinations thereof. The ceramic coating is an electrically insulating material and will typically have a thickness in the range of around 100 μm, say 10-500 μm.

Extruding and sintering or 3D printing a macroscopic structure results in a uniformly and coherently shaped macroscopic structure, which can afterwards be coated with the ceramic coating.

The electrically conductive material and the ceramic coating may have been sintered in an oxidizing atmosphere in order to form chemical bonds between the ceramic coating and the electrically conductive material; this provides for an especially high heat conductivity between the electrically conductive material and the catalytically active material supported by the ceramic coating. Thereby, the structured catalyst is compact in terms of heat transfer to the active catalytic site, and a reactor system housing the structured catalyst may be compact and limited mainly by the rate of the chemical reaction. There is no heat transfer from outside the pressure shell to the structured catalyst as would be the case through the tube walls to the catalyst within the tubes for the SMRs used in the art of steam reforming.

In an embodiment, the structured catalyst has electrically insulating parts arranged to increase the current path between the conductors to a length larger than the largest dimension of the structured catalyst. The provision of a current path between the conductors larger than the largest dimension of the structured catalyst may be by provision of electrically insulating parts positioned between the conductors and preventing the current running through some part of the structured catalyst. Such electrically insulating parts are arranged to increase the current path and thus increase the resistance through the structured catalyst. Non-limiting examples of such insulating parts are cuts, slits, bends, or holes in the electrically conductive material. Optionally, a solid insulating material such as ceramics in cuts or slits in the structure can be used. In a case where the solid insulating material is a porous ceramic material, the catalytically active material may advantageously be incorporated in the pores, by e.g. impregnation. A solid insulating material within a cut or slit assists in keeping the parts of the structured catalyst on the sides of the cut or slit from each other. As used herein, the term "largest dimension of the structured catalyst" is meant to denote the largest inner dimension of the geometrical form taken up by the structured catalyst. If the structured catalyst is box-formed, the largest dimension would be the diagonal from one corner to the farthest corner, also denoted the space diagonal.

It should be noted that even though the current through the structured catalyst may be arranged to twist or wind its way through the structured catalyst due to the electrically insulating parts arranged to increase the current path, the gas passing through the reactor system is inlet at one end of the reactor system, passes over the structured catalyst once before being outlet from the reactor system. Inert material is advantageously present in relevant gaps between the structured catalyst and the rest of the reactor system to ensure that the gas within the reactor system passes over the structured catalyst and the catalyst material herein.

In an embodiment, the length of the gas passage through the structured catalyst is less than the length of the passage of current from one electrode through the structured catalyst and to the next electrode. The ratio of the length of the gas passage to the length of the current passage may be less than 0.6, or 0.3, 0.1, or even down to 0.002.

In an embodiment, the structured catalyst has electrically insulating parts arranged to make the current path through the structured catalyst a zigzag path. Here, the terms "zigzag path" and "zigzag route" is meant to denote a path that has corners at variable angles tracing a path from one conductor to another. A zigzag path is for example a path going upwards, turning, and subsequently going downwards. A zigzag path may have many turns, going upwards and subsequently downwards many times through the structured catalyst, even though one turn is enough to make the path a zigzag path.

It should be noted that the insulating parts arranged to increase the current path are not necessarily related to the ceramic coating on the electrically conductive material; even though this ceramic coating is also considered electrically insulating, it does not change the length of the current path between the conductors connected to the electrically conductive material.

In an embodiment, the macroscopic structure has a plurality of parallel channels, a plurality of non-parallel channels and/or a plurality of labyrinthic channels, where the channels have walls defining the channels. Thereby, several different forms of the macroscopic structure can be used as long as the surface area of the structured catalyst exposed to the gas is as large as possible. In a preferred embodiment, the macroscopic structure has parallel channels, since such parallel channels render a structured catalyst with a very small pressure drop. In a preferred embodiment, parallel longitudinal channels are skewed in the longitudinal direction of the macroscopic structure. In this way, molecules of the gas flowing through the macroscopic structure will mostly tend to hit a wall inside the channels instead of just flowing straight through a channel without being in contact with a wall. The dimension of the channels should be appropriate in order to provide a macroscopic structure with a sufficient resistivity. For example, the channels could be quadratic (as seen in cross section perpendicular to the channels) and have a side length of the squares of between 1 and 3 mm; however, channels having a maximum extent in the cross section of up to about 4 cm are conceivable. The walls may e.g. have a thickness of between 0.2 and 2 mm, such as about 0.5 mm, and the ceramic coating supported by the walls has a thickness of between 10 µm and 500 µm, such as between 50 µm and 200 µm, such as 100 µm. In another embodiment, the macroscopic structure of the structured catalyst is cross-corrugated.

In general, when the macroscopic structure is extruded or 3D printed, the pressure drop from the inlet to the outlet of the reactor system may be reduced considerably compared to a reactor where the catalyst material is in the form of pellets.

In an embodiment, the reactor system further comprises a bed of a second catalyst material upstream the structured catalyst within the pressure shell. Here, the term "upstream" is seen from the flow direction of the feed gas. Thus, the term "upstream" is here meant to denote that the feed gas is directed through the bed of second catalyst material prior to reaching the structured catalyst. This provides for a situation where the second catalyst material can be arranged for pre conditioning the feed stream. No specific heating needs to be provided to the bed of second catalyst material; however, the bed of second catalyst material may be heated indirectly if it is in close proximity to the structured catalyst. Alternatively, the second catalyst material may be heated. In order to clarify the terminology used here, it is noted that the term "structured catalyst" may also be denoted "a first catalyst material" to distinguish it from the second and/or third and/or fourth catalyst material.

In an embodiment, the reactor system further comprises a third catalyst material in the form of catalyst pellets, extrudates or granulates loaded into the channels of the macroscopic structure. In this embodiment, the reactor system will thus have a catalytically active material in the coating of the macroscopic structure as well as a third catalyst material in the form catalyst pellets, extrudates or granulates within the channels of the macroscopic structure. The pellets are e.g. prepared in a dimension to loosely match the size of channels to form a single string of pellets stacked upon each other within a channel of the macroscopic structure. Alternatively, the pellets, extrudates or granulates may be prepared in a dimension significantly smaller than the channel size to form a packed bed inside each channel. As used herein, the term "pellet" is meant to denote any well-defined structure having a maximum outer dimension in the range of millimeters or centimeters, while "extrudate" and "granulate" are meant to define a catalyst material with a maximum outer dimension defined within a range.

In an embodiment a bed of fourth catalyst material is placed within the pressure shell and downstream the structured catalyst. Such fourth catalyst material may be in the form of catalyst pellets, extrudates or granulates.

In an embodiment the first, second, third, and fourth catalyst material are catalyst materials suitable for the steam reforming reaction, the prereforming reaction, or the water gas shift reaction, the dehydrogenation reaction, the methanol cracking reaction, the ammonia cracking reaction, or the hydrogen cyanide synthesis reaction. In a configuration where a combination of the second, third, and fourth catalyst material is included in the reactor system, the catalyst of each catalyst material can be different.

In an embodiment, the geometric surface area of the macroscopic structure is between 100 and 3000 $m^2/m^3$, such as between 500 and 1100 $m^2/m^3$.

In an embodiment, the material of the macroscopic structure is chosen as a material arranged to supply a heat flux of 500 $W/m^2$ to 50000 $W/m^2$ by resistance heating of the material. Preferably, resistance heating of the material supplies a heat flux of between 5 $kW/m^2$ and 12 $kW/m^2$, for example between 8 $kW/m^2$ and 10 $kW/m^2$. The heat flux is given as heat per geometric surface area of the surface exposed to the gas.

In an embodiment, the reactor system further comprises a control system arranged to control the electrical power supply to ensure that the temperature of the gas exiting the pressure shell lies in a predetermined range and/or to ensure that the conversion of the feed gas lies in a predetermined range. The control of the electrical power supply is the control of the electrical output from the power supply. The control of the electrical power supply may e.g. be carried out as a control of the voltage and/or current from the electrical power supply, as a control of whether the electrical power supply is turned on or off or as a combination hereof. The power supplied to the structured catalyst can be in the form of alternating current or direct current.

The predetermined temperature range of the gas exiting the pressure shell/the reactor system is the range from 200 to 1300° C., depending on the endothermic reaction facilitated.

In order to control the temperature of a reaction, the heat added/removed from a reactor system needs to be balanced against the heat consumed/produced by the chemical reaction. The addition/removal of heat needs to be balanced against the rate of reaction and especially the approach to equilibrium as defined by β, where β is the ratio between the reaction quotient and the equilibrium constant of a reaction. A value of β approaching 1 means the reaction mixture is close to equilibrium and values approaching 0 means the reaction mixture is far from equilibrium. In general, it is desirable to have as high a rate of reaction as possible, which is achieved at a low β, as long as the temperature can be sufficiently controlled in parallel by balancing the energy added.

In the case of the endothermic steam methane reforming reaction, heat needs to be added to ensure the reaction continues to proceed as otherwise the reaction will be equilibrated and the β value will approach 1 and the reaction will slow down. However, on the other side, it is undesirable if the temperature increases faster than the rate of reaction can follow as exposing unconverted hydrocarbons to high temperatures can result in carbon formation. A good way to follow this behavior is by the approach to equilibrium. The approach to equilibrium of the steam reforming reaction is found by initially calculating the reaction quotient (Q) of the given gas as:

$$Q = \frac{y_{CO} \cdot y_{H_2}^3}{y_{CH_4} \cdot y_{H_2O}} \cdot P^2$$

Here $y_j$ is the molar fraction of compound j, and P is the total pressure in bar. This is used to determine the equilibrium temperature ($T_{eq}$) at which the given reaction quotient is equal to the equilibrium constant:

$$Q = K_{SMR}(T_{eq})$$

where $K_{SMR}$ is the thermodynamic equilibrium constant of the steam methane reforming reaction. The approach to equilibrium of the steam methane reforming ($\Delta T_{app,SMR}$) reaction is then defined as:

$$\Delta T_{app,SMR} = T - T_{eq}$$

Where T is the bulk temperature of the gas surrounding the catalyst material used, such as the structured catalyst.

To ensure good performance of a steam reforming catalyst, it is desirable that the catalyst continuously works towards decreasing $\Delta T_{app,SMR}$. Classically, large scale industrial SMRs have been designed to obtain an approach to equilibrium of 5-20° C. at the outlet thereof.

With the current invention, it is possible to control the heat flux and match this directly to the kinetic performance of the structured catalyst, as these are independent to some extent.

In an embodiment, the structured catalyst within said reactor system has a ratio between the area equivalent diameter of a horizontal cross section through the structured catalyst and the height of the structured catalyst in the range from 0.1 to 2.0. The area equivalent diameter of the cross section through the reactor system is defined as the diameter of a circle of equivalent area as the area of the cross section. When the ratio between the area equivalent diameter and the height of the structured catalyst is between 0.1 and 2.0, the pressure shell housing the structured catalyst may be relatively small compared to other reactor systems for endothermic reactions such as the current SMRs.

Typically, the gas flows through the reactor system in an upflow or downflow direction, so that the gas flows through channels in the structured catalyst along the height thereof. When the structured catalyst comprises a number of or an array of macroscopic structures, the individual macroscopic structures within the array may be placed side by side, on top of each other or in a combination thereof. It is stressed, that when the structured catalyst comprises more than one macroscopic structures, the dimensions of the structured catalyst are the dimensions of the more than one macroscopic structures. Thus, as an example, if the structured catalyst comprises two macroscopic structures, each having the height h, put on top of each other, the height of the structured catalyst is 2 h.

The volume of the structured catalyst is chosen in consideration of the desired feed conversion and/or temperature out of the reactor system correlated to the heat generation capacity of the electrically conductive material.

In an embodiment, the height of the reactor system is between 0.5 and 7 m, more preferably between 0.5 and 3 m. Exemplary values of the height of the reactor system is a height of less than 5 meters, preferably less than 2 m or even 1 m. The dimensions of the reactor system and of the structured catalyst within the reactor system are correlated; of course, the pressure shell and heat insulation layer render the reactor system somewhat larger than the structured catalyst itself. For comparison, industrial scale SMRs are typically constructed of catalyst tubes having a length of 10 m or above to maximize external surface area of the tubes. The present invention is advantageous in that such confinement in the design of the reactor system are superfluous.

Another aspect of the invention relates to a process for carrying out an endothermic reaction of a feed gas in a reactor system comprising a pressure shell housing a structured catalyst arranged for catalyzing the endothermic reaction of a feed gas. The structured catalyst comprises a macroscopic structure of electrically conductive material, where the macroscopic structure supports a ceramic coating, and where the ceramic coating supports a catalytically active material. The reactor system is provided with heat insulation between the structured catalyst and the pressure shell. The process comprises the following steps:

pressurizing a feed gas to a pressure of at least 2 bar,
supplying said pressurized feed gas to the reactor system,
allowing the feed gas to undergo the endothermic reaction over the heated structured catalyst and outletting a product gas from the reactor system, and
supplying electrical power via electrical conductors connecting an electrical power supply placed outside said pressure shell to said structured catalyst, allowing an electrical current to run through said macroscopic structure material, thereby heating at least part of the structured catalyst to a temperature of at least 200° C.

The process provides advantages similar to those outlined for the reactor system. However, the process may comprise further steps carried out on the product gas, such as purification, pressurization, heating, cooling, etc. to provide the final product gas for an application downstream the reactor system of this invention.

It should be noted that the feed gas may comprises individual feed gasses and that the step of pressurizing the feed gas may comprise pressurizing individual feed gasses individually. Moreover, it should be noted that the order in which the steps of the process are written are not necessarily the order in which the process steps take place, in that two or more steps may take place simultaneously, or the order may be different that indicated above.

In an embodiment, the process comprises the step of pressurizing the gas upstream the pressure shell to a pressure of up to at least 2 bar. The chosen operating pressure is defined by the endothermic reaction and the integration of the reactor in the surrounding process steps.

In an embodiment of the process according to the invention, the temperature of the feed gas let into the reactor system is between 100° C. and 700° C. However, in all embodiments the temperature and the pressure of the feed gas are adjusted to ensure that the feed gas is above the dew point.

In an embodiment of the process of the invention, the structured catalyst is heated so that the maximum temperature of the structured catalyst lies between 200° C. and 1300° C. The used temperature will be dependent on the endothermic reaction. The maximum temperature of the structured catalyst depends upon the material of the electrically conductive material; thus, if the electrically conductive material is of FeCrAlloy, which melts at a temperature of between 1380° C. and 1490° C. (depending on the actual alloy), the maximum temperature should be somewhat below the melting point, such as at about 1300° C. if the melting point of the electrically conductive material is at about 1400° C., as the material will become soft and ductile when approaching the melting point. The maximum temperature may additionally be limited by the durability of the catalyst material, the coating and the catalytically active material.

In an embodiment the process according to the invention further comprises the step of inletting a cooling gas through an inlet through the pressure shell in order to allow a cooling gas to flow over at least one conductor and/or fitting. The cooling gas may advantageously be hydrogen, nitrogen, steam, carbon dioxide or any other gas suitable for cooling the area or zone around the at least one conductor. A part of the feed gas may be fed to the pressure shell as the cooling gas.

In an embodiment according to the invention, the process further comprises the step of inletting a cooling gas through an inlet through the pressure shell in order to allow a cooling gas to flow over at least one conductor and/or fitting. The cooling gas may be any appropriate gas; examples of such gasses are hydrogen, nitrogen, steam, carbon dioxide or mixtures thereof. The cooling gas may flow through the conductor(s) and cool it (them) from within; in this case, the conductor(s) need(s) to be hollow to accommodate the cooling gas flowing within it/them.

In an embodiment, the endothermic reaction is dehydrogenation of hydrocarbons. This reaction takes place according to reaction (viii). The catalyst material for the reaction may be $Pt/Al_2O_3$ or $Pt—Sn/Al_2O_3$. The catalytically active material may be Pt. The maximum temperature of the reactor may be between 500-700° C. The pressure of the feed gas may be 2-5 bar.

In an embodiment, the endothermic reaction is cracking of methanol. This reaction takes place according to reaction (v), (ix), and (x). The catalyst material for the reaction may be $Ni/MgAl_2O_3$ or $Cu/Zn/Al_2O_3$. The catalytically active material may be Cu or Ni. The maximum temperature of the reactor may be between 200-300° C. The pressure of the feed gas may be 2-30 bar, preferably about 25 bar.

In an embodiment, the endothermic reaction is steam reforming of hydrocarbons. This reaction takes place according to reaction (i)-(v). The catalyst material for the reaction may be $Ni/Al_2O_3$, $Ni/MgAl_2O_3$, $Ni/CaAl_2O_3$, $Ru/MgAl_2O_3$, or $Rh/MgAl_2O_3$. The catalytically active material may be Ni, Ru, Rh, Ir, or a combination thereof. The maximum temperature of the reactor may be between 850-1300° C. The pressure of the feed gas may be 15-180 bar, preferably about 25 bar.

In an embodiment, the endothermic reaction is ammonia cracking. This reaction takes place according to reaction (xi). The catalyst material for the reaction may be Fe, FeCo, or $Ru/Al_2O_3$. The catalytically active material may be Fe or Ru. The maximum temperature of the reactor may be between 400-700° C. The pressure of the feed gas may be 2-30 bar, preferably about 25 bar.

In an embodiment, the endothermic reaction is the hydrogen cyanide synthesis or a synthesis process for organic nitriles. This reaction takes place according to reaction (vi) and (vii). The catalyst material for the reaction may be $Pt/Al_2O_3$. The catalytically active material may be Pt, Co, or SnCo. The maximum temperature of the reactor may be between 700-1200° C. The pressure of the feed gas may be 2-30 bar, preferably about 5 bar.

In an embodiment, the endothermic reaction is aromatization of hydrocarbons. This is advantageously aromatization of higher hydrocarbons.

The following is a detailed description of embodiments of the invention depicted in the accompanying drawings. The embodiments are examples and are in such detail as to clearly communicate the invention. However, the amount of detail offered is not intended to limit the anticipated variations of embodiments; but on the contrary, the intention is to cover all modifications, equivalents, and alternatives falling within the spirit and scope of the present invention as defined by the appended claims.

SHORT DESCRIPTION OF THE FIGURES

FIGS. 3a and 3b show schematic cross sections through an embodiment of the inventive reactor system comprising a structured catalyst;

DETAILED DESCRIPTION OF THE FIGURES

Throughout the Figures, like reference numbers denote like elements.

Figure 1A:
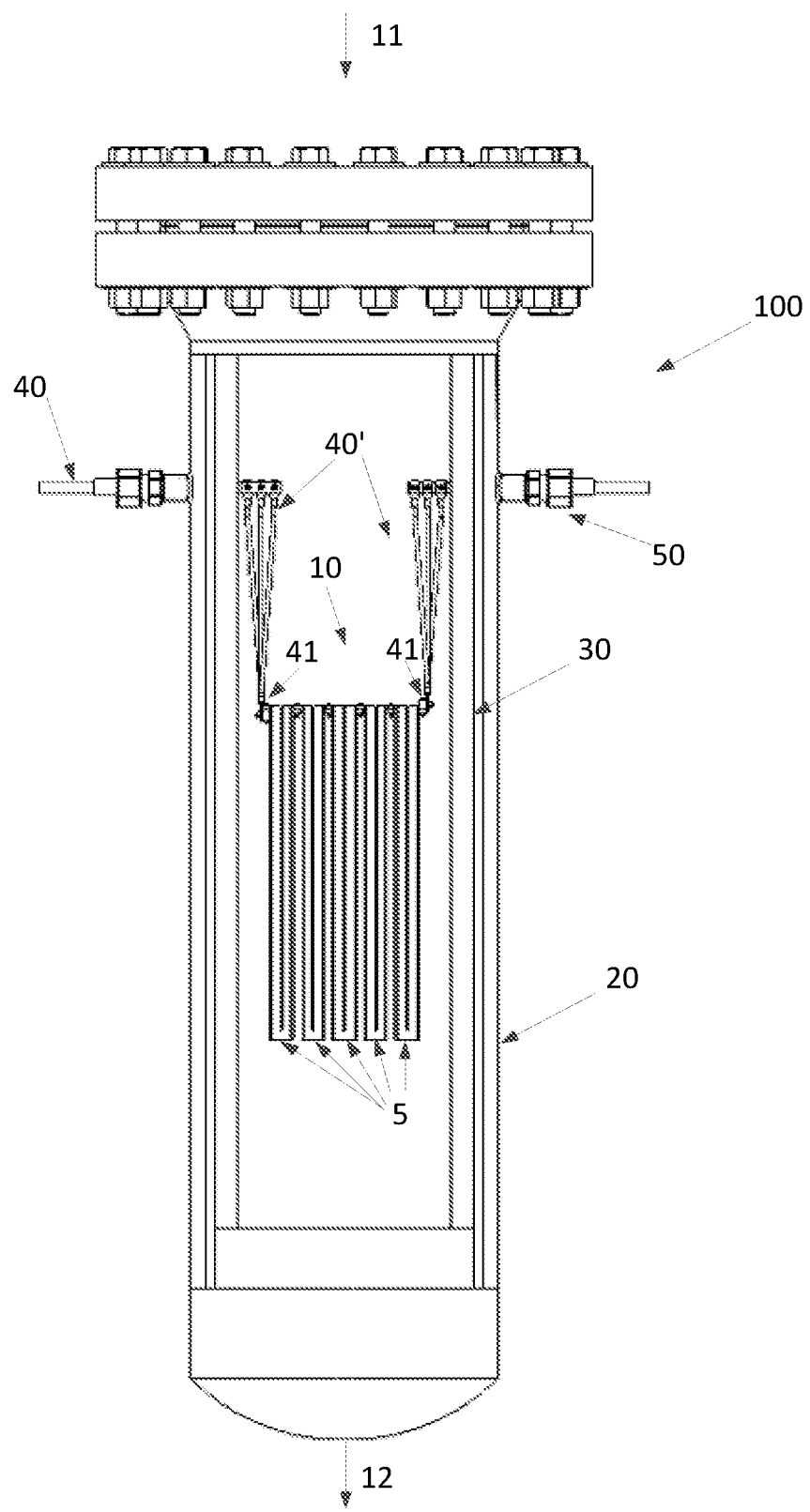
FIG. 1a shows a cross section through an embodiment of the inventive reactor system with a structured catalyst comprising an array of macroscopic structures, in a cross section.

FIG. 1a shows a cross section through an embodiment of a reactor system 100 according to the invention. The reactor system 100 comprises a structured catalyst 10, arranged as an array of macroscopic structures 5. Each macroscopic structure 5 in the array is coated with a ceramic coating impregnated with catalytically active material. The reactor system 100 moreover comprises conductors 40, 40' connected to a power supply (not shown in the FIGURES) and to the structured catalyst 10, viz. the array of macroscopic structures. The conductors 40, 40' are led through the wall of a pressure shell 20 housing the structured catalyst and through insulating material 30 on the inner side of the pressure shell, via fittings 50. The conductors 40' are connected to the array of macroscopic structures 5 by conductor contact rails 41.

In an embodiment, the electrical power supply supplies a voltage of 26V and a current of 1200 A. In another embodiment, the electrical power supply supplies a voltage of 5V and a current of 240 A. The current is led through electrical conductors 40, 40' to conductor contact rails 41, and the current runs through the structured catalyst 10 from one conductor contact rail 41, e.g. from the conductor contact rail seen to the left in FIG. 1*a*, to the other conductor contact rail 41, e.g. the conductor contact rail seen to the right in FIG. 1*a*. The current can be both alternating current, and e.g. run alternating in both directions, or direct current and run in any of the two directions.

The macroscopic structures 5 are made of electrically conductive material. Especially preferred is the alloy kanthal consisting of aluminum, iron and chrome. The ceramic coating, e.g. an oxide, coated onto the structure catalysts 5 is impregnated with catalytically active material. The conductors 40, 40' are made in materials like iron, aluminum, nickel, copper or alloys thereof.

During operating, a feed gas enters the reactor system 100 from above as indicated by the arrow 11 and exits the reactor system from the bottom thereof as indicated by the arrow 12.

Figure 1B:
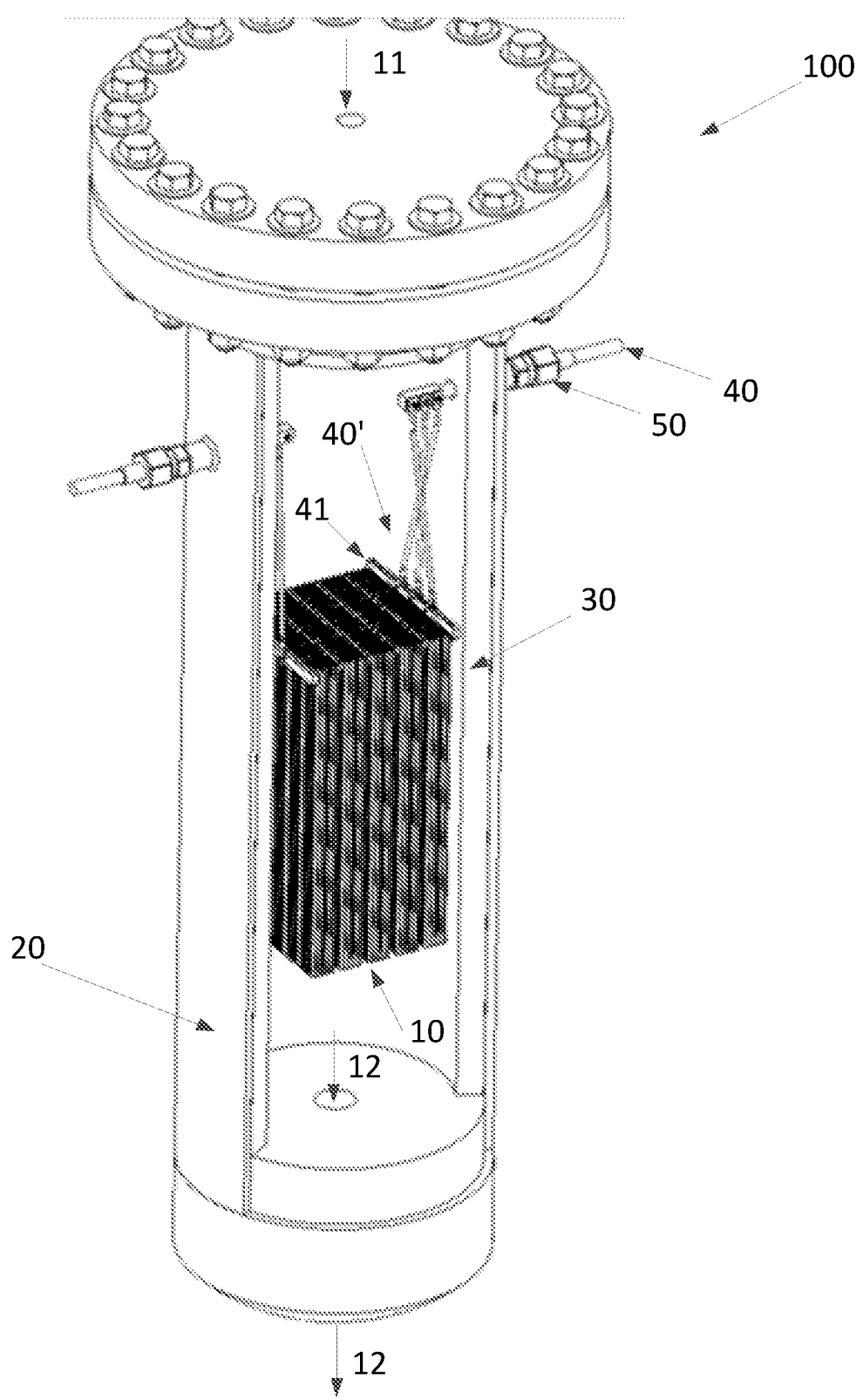
FIG. 1b shows the reactor system of FIG. 1a with a part of the pressure shell and heat insulation layer removed.
Figure 2:
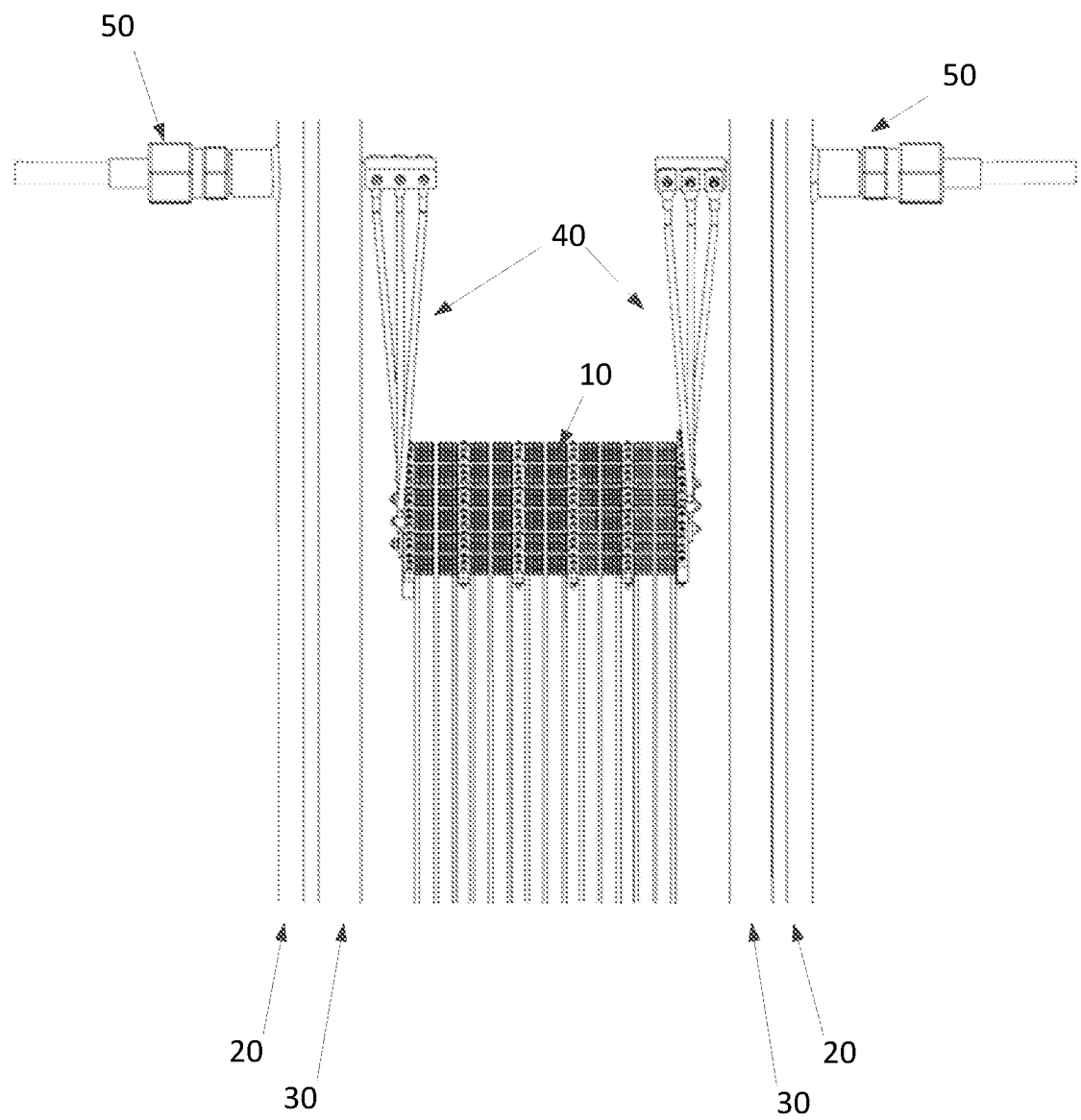
FIG. 2 is an enlarged view of a part of the reactor system.

FIG. 1*b* shows the reactor system 100 of FIG. 1*a* with a part of the pressure shell 20 and heat insulation 30 layer removed and FIG. 2 is an enlarged view of a part of the reactor system 100. In FIGS. 1*b* and 2 the connections between conductors 40' and conductor contact rails 41 are shown more clearly than in FIG. 1*a*. Moreover, it is seen that the conductors 40 are led through the walls of the pressure shell in a fitting 50, and that the one conductor 40 is split up into three conductors 40' within the pressure shell. It should be noted, that the number of conductors 40' may be any appropriate number, such as smaller than three or even larger than three.

In the reactor system shown in FIGS. 1*a*, 1*b* and 2, the conductors 40, 40' are led through the wall of a pressure shell 20 housing the structured catalyst and through insulating material 30 on the inner side of the pressure shell, via fittings 50. Feed gas for steam reforming is inlet into the reactor system 100 via an inlet in the upper side of the reactor system 100 as shown by the arrow 11, and reformed gas exists the reactor system 100 via an outlet in the bottom of the reactor system 100 as shown by the arrow 12. Moreover, one or more additional inlets (not shown in FIGS. 1*a* to 2) advantageously exist close to or in combination with the fittings 50. Such additional inlets allow a cooling gas to flow over, around, close to, or inside at least one conductor within the pressure shell to reduce the heating of the fitting. The cooling gas could e.g. be hydrogen, nitrogen, steam, carbon dioxide or mixtures thereof. The temperature of the cooling gas at entry into the pressure shell may be e.g. about 100° C.

In the reactor system 100 shown in FIGS. 1*a* to 2, inert material (not shown in FIGS. 1*a*-2) is advantageously present between the lower side of the structured catalyst 10 and the bottom of the pressure shell. Moreover, inert material is advantageously present between the outer sides of the structured catalyst 10 of macroscopic structures 5 and the insulating material 30. Thus, one side of the insulating material 30 faces the inner side of the pressure shell 20 and the other side of the insulating material 30 faces the inert material. The inert materiel is e.g. ceramic material and may be in the form of pellets. The inert material assists in controlling the pressure drop across the reactor system 100 and in controlling the flow of the gas through the reactor system 100, so that the gas flows over the surfaces of the structured catalyst 10.

FIGS. 3*a* and 3*b* show schematic cross sections through an embodiment of the inventive reactor system 100', 100" comprising a structured catalyst 10'. The structured catalyst 10' may consist of a single macroscopic structure with ceramic coating supporting catalytically active material or it may contain two or more macroscopic structures. Each of the reactor systems 100', 100" comprises a pressure shell 20 and a heat insulation layer 80 between the structured catalyst 10' and the pressure shell 20. Inert material 90 can be used to fill the gap between the structured catalyst 10' and the heat insulation layer or the pressure shell 20. In FIGS. 3*a* and 3*b*, the inert material 90 is indicated by dotted area; the inert material 90 may be in any appropriate form, e.g. in the form of inert pellets, and it is e.g. of ceramic material. The inert material 90 assists in controlling the pressure drop through the reactor system and in controlling the flow of the gas through the reactor system. Moreover, the inert material typically has a heat insulating effect.

From FIGS. 3*a* and 3*b* it is seen that the reactor systems 100', 100" further comprise an inner tube 15 in heat exchange relationship with the structured catalyst 10'. The inner tube 15 is adapted to withdraw a product gas from the structured catalyst 10' so that the product gas flowing through the inner tube or tubes is in heat exchange relationship with the gas flowing over the structured catalyst; however, the inner tube 15 is electrically insulated from the structured catalyst 10' by either a heat insulation layer 80, inert material 90, a gap, or a combination. This is a layout which is denoted a bayonet reactor system. In this layout, the product gas within the inner tube assists in heating the process gas flowing over the macroscopic structure. In the layouts shown in FIGS. 3*a* and 3*b*, the feed gas enters the reactor system 100', 100" as indicated by the arrow 11, and continues into the structured catalyst 10' as indicated by the arrows 13. During the passage of the feed gas over the structured catalyst 10', it undergoes the steam reforming reaction. The gas exiting the structured catalyst 10' is at least partly reformed. The at least partly reformed gas flows from the structured catalyst 10' into the inner tube 15 as indicated by the arrows 14, and exits the inner tube as indicated by the arrows 12. Even though the heat insulation layer 80 is present between the inner tube 15 and the structured catalyst 10', some heat transfer will take place from the gas within the inner tube 15 and the gas within the structured catalyst 10' or upstream the structured catalyst 10'. In the embodiments shown in FIGS. 3*a* and 3*b*, the feed gas flow downwards through the structured catalyst 10' and upwards through the inner tube 15; however, it is conceivable that the configuration was turned upside-down so that the feed gas would flow upwards through the structured catalyst 10' and downwards through the inner tube 15.

Figure 4:
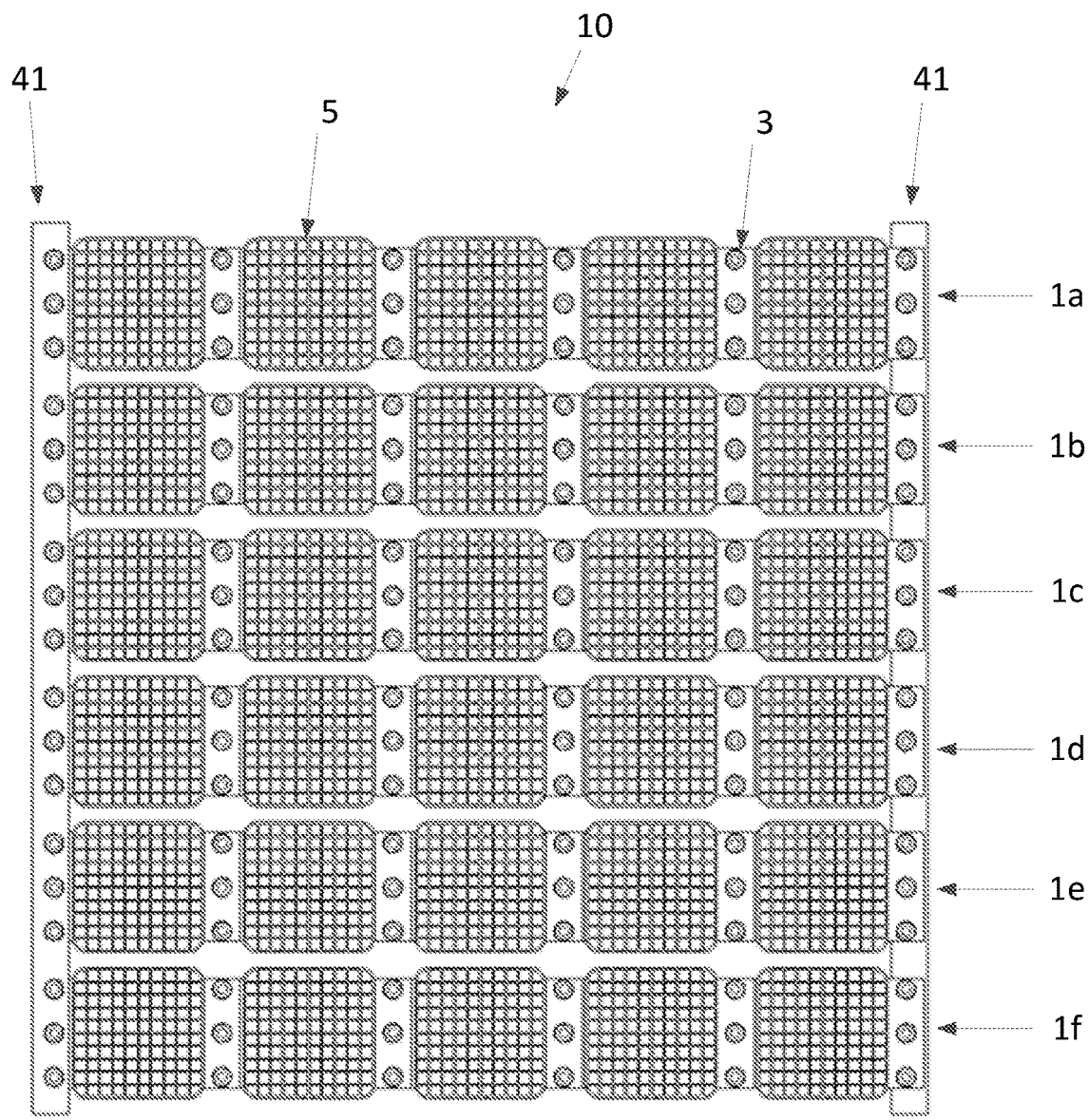
FIGS. 4 and 5 show an embodiment of a structured catalyst with an array of macroscopic structures as seen from above and from the side, respectively.
Figure 5:
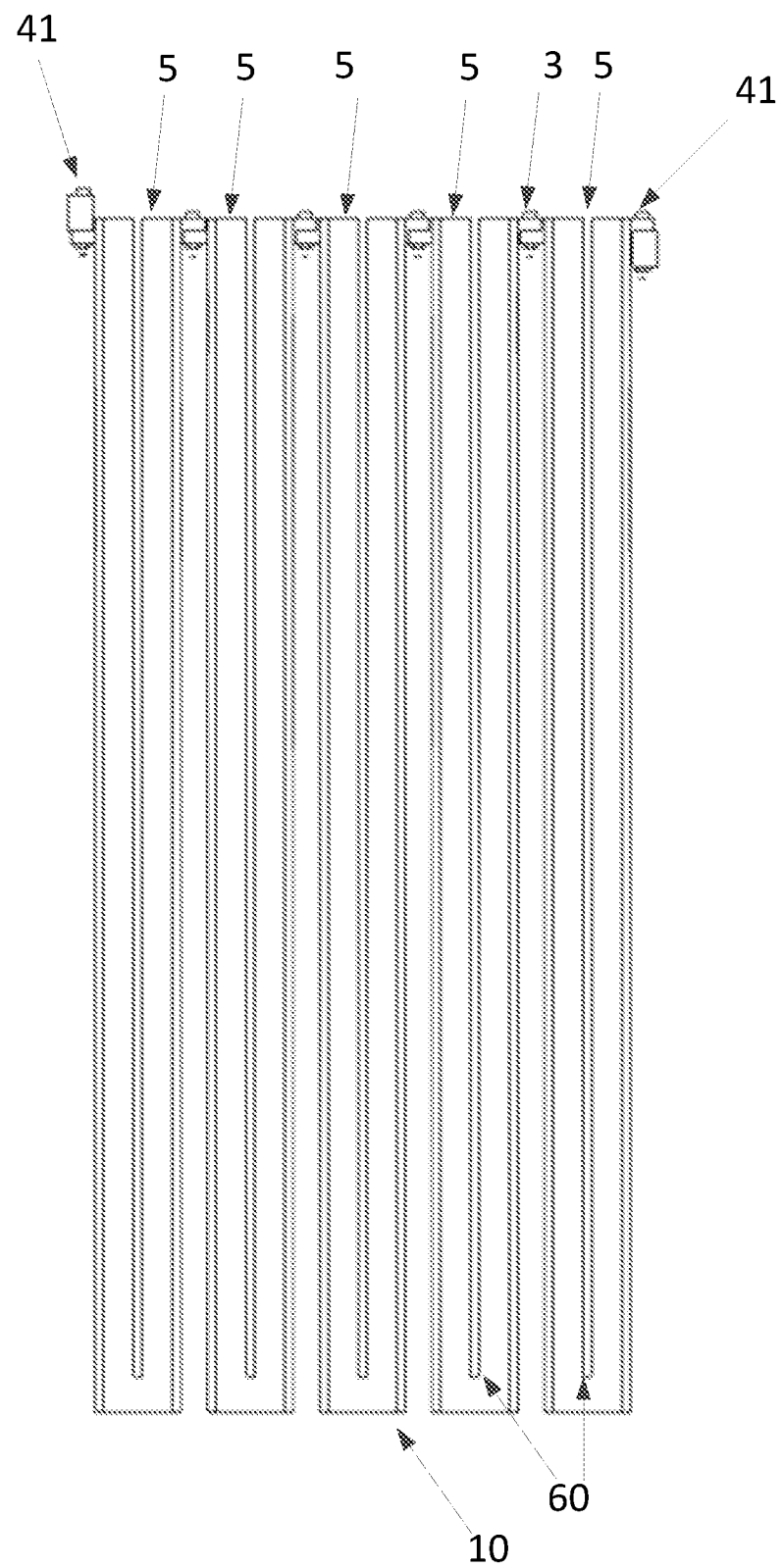

FIGS. 4 and 5 show an embodiment of a structured catalyst comprising an array of macroscopic structures as seen from above and from the side, respectively. FIG. 4 shows a structured catalyst 10 comprising an array of macroscopic structure 5 seen from above, viz. as seen from the arrow 11 in FIGS. 1*a* and 1*b*. The array has 6 rows, viz. 1*a*, 1*b*, 1*c*, 1*d*, 1*e* and 1*f*, of five macroscopic structures 5. The macroscopic structures 5 in each row are connected to its neighboring macroscopic structure (s) in the same row and the two outermost macroscopic structures in each row are connected to a conductor contact rail 41. The neighboring macroscopic structure 5 in a row of macroscopic structures are connected to each other by means of a connection piece 3.

FIG. 5 shows the structured catalyst 10 having an array of macroscopic structures 5 of FIG. 4 seen from the side. From FIG. 5, it can be seen that each macroscopic structure 5 extends longitudinally perpendicular to the cross section seen in FIG. 4. Each macroscopic structure 5 has a slit 60 cut into it along its longitudinal direction (see FIG. 5). Therefore, when energized by the power source, the current enters the array of macroscopic structures 5 via a conductor contact rail 41, is led through the first macroscopic structure 5 downwards until the lower limit of the slit 60 and is subsequently led upwards towards a connection piece 3. The current is led via a corresponding zigzag path, downwards and upwards, through each macroscopic structure 5 in each row 1a-1f of macroscopic structures 5 in the array 10. This configuration advantageously increases the resistance over the structured catalyst 10.

Figure 6:
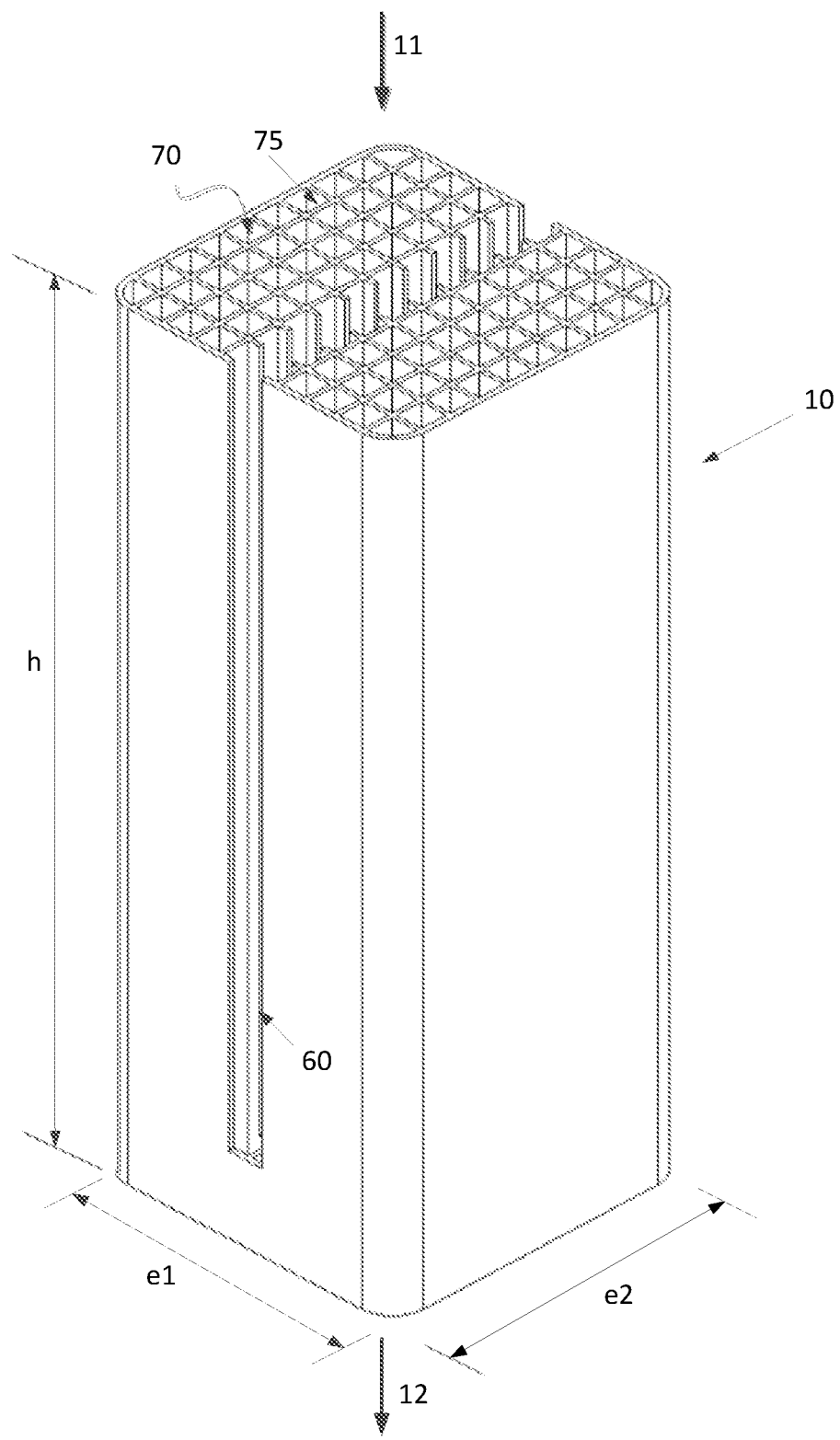
FIG. 6 shows an embodiment of the structured catalyst of the invention.

FIG. 6 shows a structured catalyst 10 according to the invention in a perspective view. The structured catalyst 10 comprises a macroscopic structure that is coated with a ceramic coating impregnated with catalytically active material. Within the structured catalyst are channels 70 extending along the longitudinal direction (shown by the arrow indicate 'h' in FIG. 6) of the macroscopic structure 5; the channels are defined by walls 75. In the embodiment shown in FIG. 6, the walls 75 define a number of parallel, square channels 70 when seen from the direction of flow as indicated by the arrow 12. The structured catalyst 10 has a substantially square perimeter when seen from above, defined by the edge lengths e1 and e2. However, the perimeter could also be circular or another shape.

The walls 75 of the structured catalyst 10 are of extruded or 3D printed material coated with a ceramic coating, e.g. an oxide, which has been coated onto the macroscopic structure. In the Figures, the ceramic coating is not shown. The ceramic coating is impregnated with catalytically active material. The ceramic coating and thus the catalytically active material are present on every walls within the structured catalyst 10 over which the gas flow flows during operation and interacts with the heated surface of the structured catalyst and the catalytically active material.

Thus, during use in a reactor system for steam reforming, a hydrocarbon feed gas flows through the channels 70 and interacts with the heated surface of the structured catalyst and with the catalytically active material supported by the ceramic coating.

In the structured catalyst 10 shown in FIG. 6 a slit 60 has been cut into the structured catalyst 10. This slit 60 forces a current to take a zigzag route, in this instance downwards and subsequently upwards, within the macroscopic structure thereby increasing the current path and thus the resistance and consequently the heat dissipated within the macroscopic structure. The slit 60 within the macroscopic structure may be provided with embedded insulating material in order to ensure that no current flows in the transverse direction of the slit 60.

The channels 70 in the structured catalyst 10 are open in both ends. In use of the structured catalyst in a reactor system, a hydrocarbon feed gas flows through the unit, in the direction shown by arrows 11 and 12 in FIGS. 1a and 1b, and gets heated via contact with the walls 75 of the channels 70 and by heat radiation. The heat initiates the desired steam reforming process. The walls 75 of the channels 70 may e.g. have a thickness of 0.5 mm, and the ceramic coating coated onto the walls 75 may e.g. have a thickness of 0.1 mm. Even though the arrows 11 and 12 (see FIGS. 1a and 1b) indicate that the flow of the hydrocarbon feed gas is down-flow, the opposite flow direction, viz. an up-flow, is also conceivable.

Figure 7:
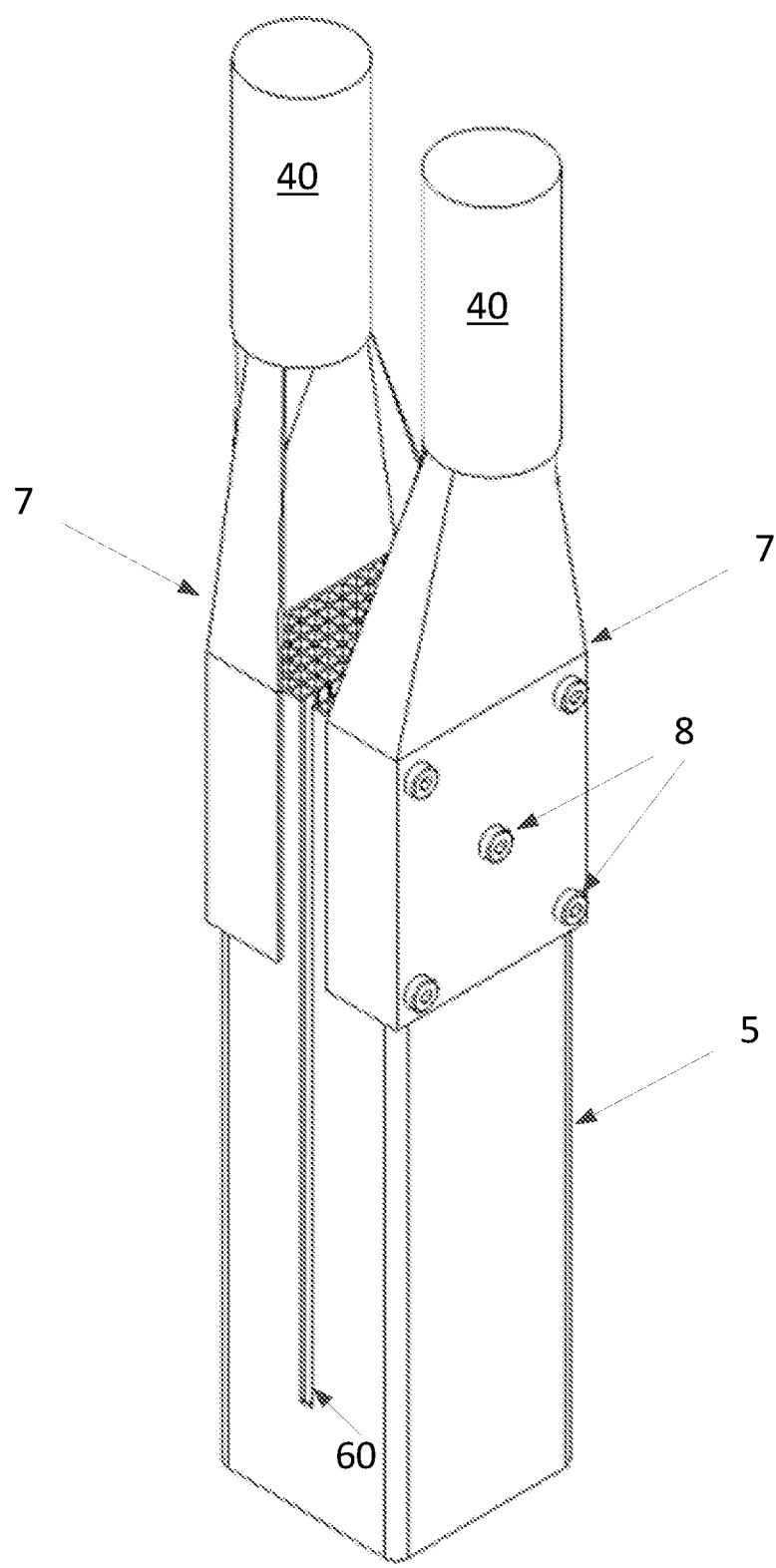
FIGS. 7, 8 and 9 shows embodiments of a structured catalyst with connectors.

FIG. 7 shows the structured catalyst 10 of FIGS. 1a and 1b in a perspective view and with connectors 7 attached. The connectors 7 each connects a part of the structured catalyst 10 to a conductor 40. The conductors 40 are both connected to a power supply (not shown). Each of the connectors 7 are connected to an upper part of the structured catalyst. When the conductors 40 are connected to a power supply, an electrical current is led to the corresponding connector 7 via the conductor and runs through the structured catalyst 10. The slit 60 hinders the current flow in a transverse direction (horizontal direction of FIG. 7) throughout its lengths along the height h of the structured catalyst 10. Therefore, the current runs in a direction downwards as seen in FIG. 7 in the part of the structured catalyst along the slit 60, subsequently it runs transversely to the longitudinal direction below the slit 60 as seen in FIG. 7 and finally the current runs upwards in the longitudinal direction of the structured catalyst to the other connector 7. The connectors 7 in FIG. 7 are mechanically fastened to the structured catalyst by means of i.a. mechanical fastening means such as screws and bolts. However, additional or alternative fastening means are conceivable. In an embodiment, the electrical power supply generates a voltage of 3V and a current of 400 A. The connectors 7 are e.g. made in materials like iron, aluminum, nickel, copper or alloys thereof.

As mentioned, the structured catalyst 10 is coated with a ceramic coating, such as an oxide, supporting the catalytically active material. However, the parts of the structured catalyst 10, which are connected to the connectors 7, should not be coated with an oxide. Instead, the macroscopic structure of the structured catalyst should be exposed or connected directly to the connectors 7 in order to obtain a good electrical connection between the macroscopic structure and the connector.

When the connectors 7 and thus the conductors 40 are connected to the same end of the structured catalyst 10, viz. the upper end as seen in FIG. 7, the gas entering into a reactor system housing the structured catalyst 10 would be able to cool the connectors 7 and the conductors 40. For instance, the hydrocarbon gas entering into such a reactor system would have a temperature of 400° C. or 500° C. and would thus keep the connectors 7 and conductors 40 from reaching temperatures much higher than this temperature.

Figure 8:
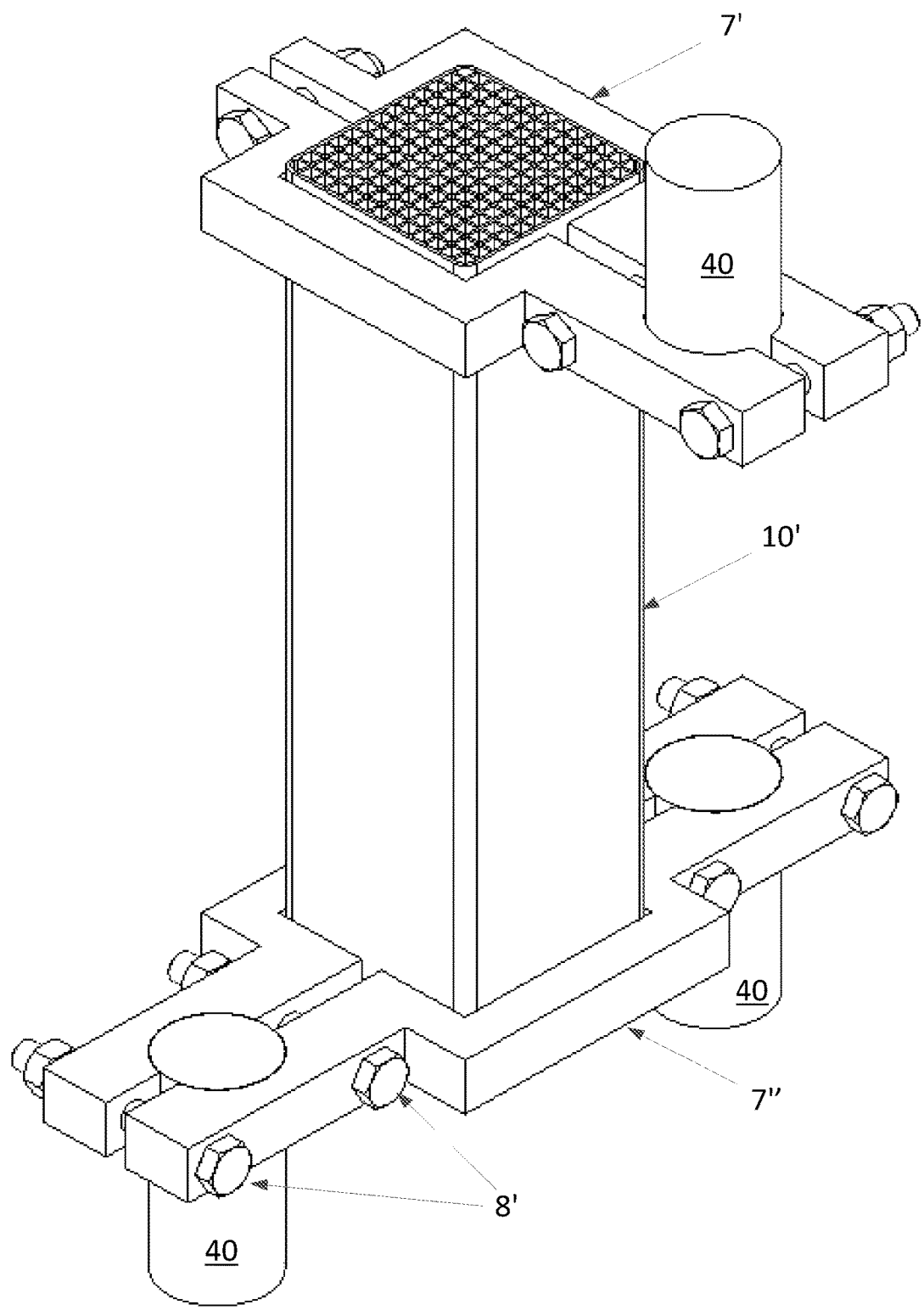

FIG. 8 shows an alternative embodiment of the structured catalyst 10' with connectors 7' attached. The structured catalyst 10' shown in FIG. 8 has a square cross section, like the structured catalyst 10 shown in FIGS. 6 and 7; however, the structured catalyst 10' of FIG. 8 does not have any slit cut through it. In the upper and lower end of the macroscopic structure 10' a conductor 40. The material of the conductor 40 is e.g. nickel. Alternatively, other appropriate metals could be used as electrical current distributors, or alloys such as FeCrAlloy. Connectors 7', 7" in the form of electrical conducting bars are used for guiding the current across the structured catalyst 10', i.e. the macroscopic structure. The connectors 7', 7" are fastened to the conductors 40 and to the structured catalyst 10' by use of mechanical fastening means; however, alternative or additional fastening means are also conceivable.

Connectors 7" at the lower end of the structured catalyst 10' may be made of a different material compared to the connectors 7' at the upper end of the structured catalyst 10' as seen in FIG. 2. For example, the connectors 7' may be of cupper, whilst the connectors 7" may be of nickel. Since nickel has a lower conductivity than cupper, the connectors 7" are larger than the connectors 7'.

The embodiment shown in FIG. 8 is suitable for temperatures below 800° C., such as 600-700° C.

Figure 9:
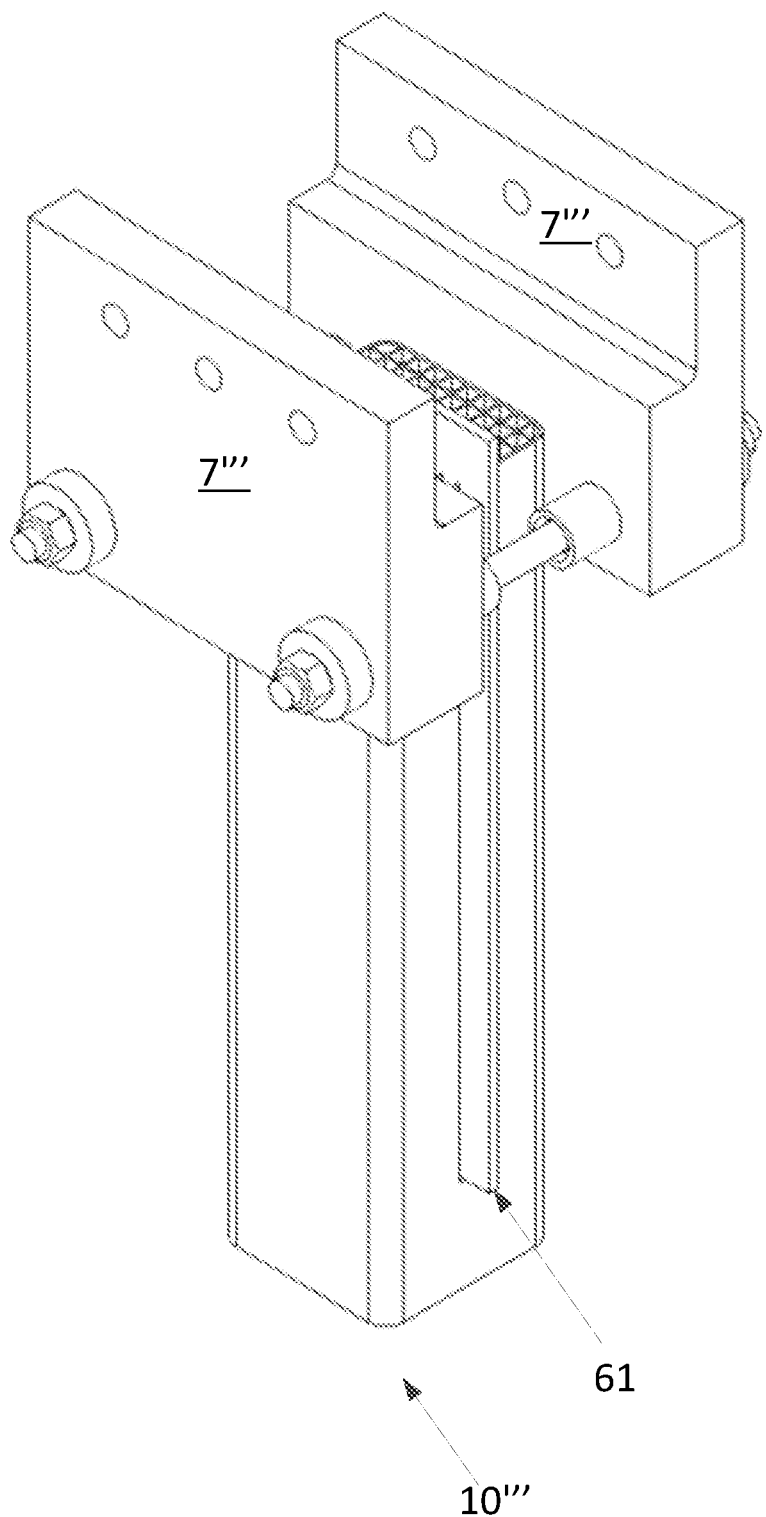

FIG. 9 shows another embodiment of a structured catalyst 10''' with connectors 7'''. The structured catalyst 10''' is e.g. the structured catalyst as shown in FIG. 6. Each of the connectors T" has three holes at an upper side thereof for connection to conductors (not shown). A piece of electrically insulating material 61 is inside the slit 60 (see FIG. 6) of the structured catalyst 10".

Figure 10:
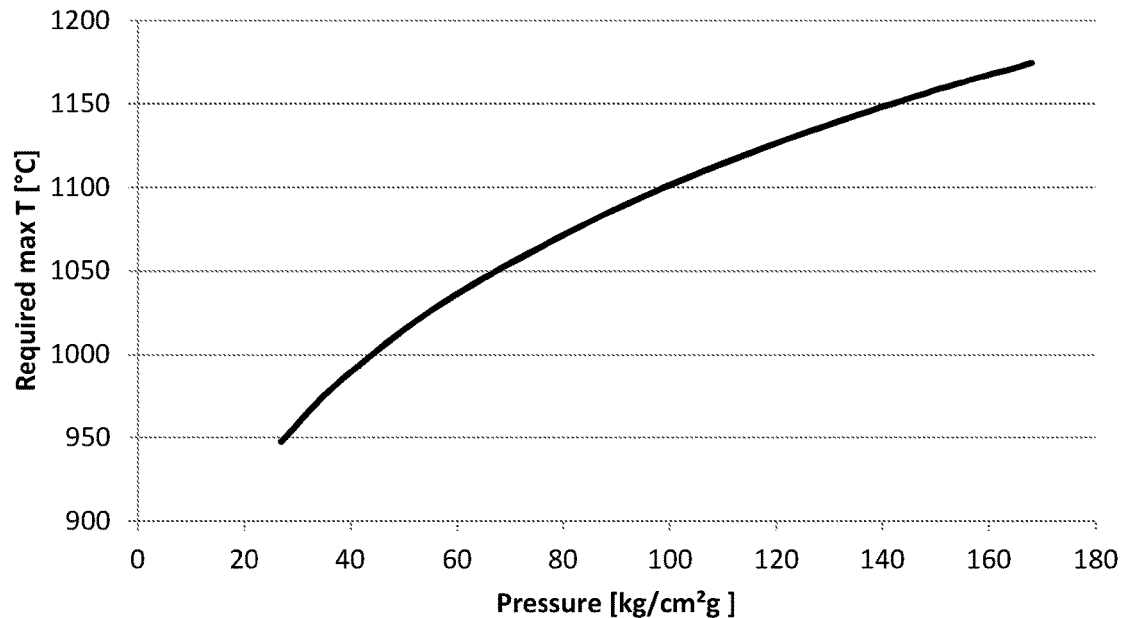
FIG. 10 shows the required maximum temperature within the reactor system of the invention as a function of the pressure.

FIG. 10 shows the required maximum temperature within the reactor system of the invention as a function of the pressure for pressures of about 30 bar to about 170 bar during steam reforming of a feed gas consisting of 30.08% $CH_4$, 69.18% $H_2O$, 0.09% Hz, 0.45% $CO_2$, 0.03% Ar, 0.02% CO, 0.15% $N_2$ to a methane conversion of 88% at a 10° C. approach to the steam methane reforming equilibrium. The required maximum temperature increases with pressure due to Le Chatelier's principle. This shows that the high temperatures which can be used in the current invention allows for using pressures which are significantly higher than the pressures used in a traditional SMR, where the external heating of the tubes prohibit the temperature exceeding ca. 950° C. A temperature of 950° C. corresponds to 27 barg in FIG. 10. In a reactor system of the invention, a maximum temperature of e.g. 1150° C. can be used which allows for a pressure of up to 146 barg with the same conversion of methane as indicated above.

Figure 11:
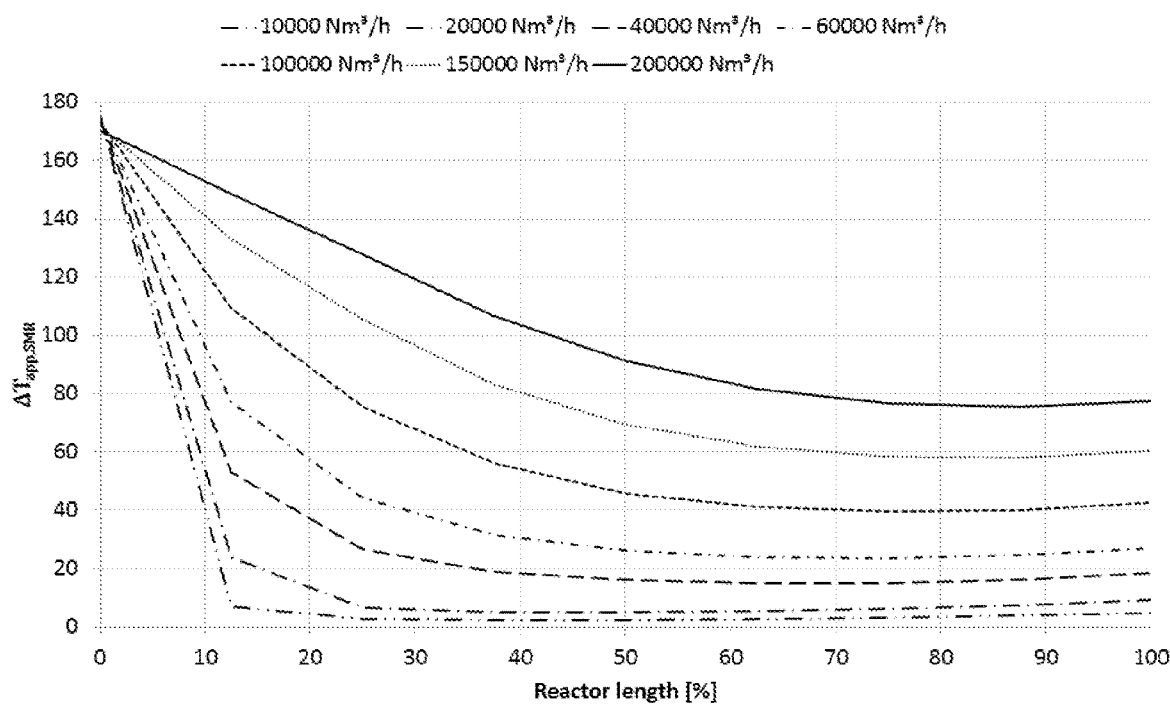
FIG. 11 is a graph of the approach to equilibrium ($\Delta T_{app, SMR}$) of the steam methane reforming reaction for different gas flow rates over a structured catalyst.

A general trend in all the curves in the FIG. 11 is that the approach to equilibrium is continuously decreasing from the entry into the structured catalyst until a pseudo equilibrium is reached, where the heat added and the heat consumed roughly equal each other. The approach to equilibrium from this stage is substantially constant or has a slightly increasing development due to the overall increasing temperature of the reactor system. For e.g. the flow rate 150 000 Nm³/h, the approach to equilibrium goes below 60° C. at about 80% of the reactor system length, but subsequently increases to about 60° C.

EXAMPLES

While the invention has been illustrated by a description of various embodiments and examples while these embodiments and examples have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicant's general inventive concept.

All the examples described below relate to compact reactor systems. This is possible due to the reactor systems comprise compact structured catalysts having a high thermal flux when powered by a power source. It is moreover to be noted, that the dimensions of the structured catalysts may be chosen relatively freely, so that the structured catalyst may be almost cubic in outer shape or it may be wider than its height.

The examples all describe operation conditions with high pressure, ranging from 28 bar to 182 bar. Such high pressures are made possible by the configuration of the reactor system since the structured catalyst within the reactor system has high thermal flux upon powering by a power source, is to some extent thermally insulated from the pressure shell, and the pressure drop through the structured catalyst is very low or even non-existing. The structured catalyst will obtain the highest temperature within the reactor system, while the pressure shell will have a significantly lower temperature due to the thermal insulation between the macroscopic structure and the pressure shell. Ideally, the temperature of the pressure shell will not exceed 500° C. When product gas with a high pressure is needed, such as 30 bar or above, the product gas exiting the reactor system can in many cases be used directly, without the use of compressors. This is due to the possibility of pressurizing the feed gas upstream the reactor system of the invention.

In all the examples described below, steam reforming is used as example where the feed gas enters the reactor system and flows over the structured catalyst housed therein. When the heat insulation layer of the reactor system is a heat insulating material, the heat insulating material typically makes up most of the space between the structured catalyst and the pressure shell along the walls of the pressure shell so that the feed gas is forced to flow along walls of the macroscopic structure on its way through the pressure shell.

The examples below (except for the comparative example) all relate to a reactor system with a structured catalyst for steam reforming. The structured catalysts described in these examples comprise one or more macroscopic structures. The one or more macroscopic structures of the examples below all support a ceramic coating supporting catalytically active material. Advantageously, substantially all the surface of the macroscopic structure supports the ceramic coating supporting the catalytically active material; however, at connections points, e.g. between two adjacent macroscopic structures or between a macroscopic structure and a conductor, the macroscopic structure may be free from ceramic coating in order to facilitate connection between a conductor and the macroscopic structure.

Example 1

An example calculation of the process of the invention is given in Table 1 below. A hydrocarbon feed stream comprising i.a. a hydrocarbon gas, hydrogen and steam is fed to the reactor system of the invention. The feed stream entering the reactor system is pressurized to a pressure of 28 kg/cm²·g and has a temperature of 500° C. Inside the reactor system, a structured catalyst in the form of nine macroscopic structures having a square cross section are placed in an array and each macroscopic structure has a size of 0.53 times 0.53 times 2.3 meter. Each macroscopic structure additionally has 17778 channels with a square cross section having a side or edge length of 0.32 cm. Each macroscopic structure has slits parallel to the longitudinal direction thereof, so that clusters of 5 times 5 channels are formed. The clusters are individually insulated from the neighboring cluster, except from the ends, so that the current path through the structured catalyst is a zigzag path. A current of 200 A and a voltage of ca. 5.5 kV are applied to each macroscopic structure of the reactor system of the invention in order to heat the structured catalyst and thus the gas passing over the structured catalyst, corresponding to a power supplied in the structured catalysts of 9899 kW.

The reactor system in the current configuration could have an overall internal diameter of the reactor system of 3.2 m and a total internal height of 5.5 m when the reactor system is made as a cylindrical reactor system with spherical heads. In this specific configuration, the macroscopic structures are placed in a square orientation having a diagonal length of 2.3 m. In all the examples described herein, except for the comparative example, inert material is placed around the structured catalyst(s) to close the gap to the insulation material, adjacent to the pressure shell. The insulation material in example 1 has a cylindrical form with an internal diameter of 2.5 m and a thickness of 0.35 m.

During the passage of the feed gas through the reactor system, the feed gas is heated by the structured catalyst and undergoes steam reforming to a product gas having an exit temperature of 963° C.

TABLE 1

Size of structured catalyst:

| | |
|---|---|
| Edge size [m] | 0.53 |
| Height [m] | 2.3 |
| Number of macroscopic structures | 9 |
| Total volume [L] | 5888 |

| | Feed gas | Product gas |
|---|---|---|
| T [° C.] | 500 | 963 |
| P [kg/cm$^2$ g] | 27.97 | 27.47 |
| CO2 [Nm$^3$/h] | 168 | 727 |
| N2 [Nm$^3$/h] | 26 | 26 |
| CH4 [Nm$^3$/h] | 2630 | 164 |
| H2 [Nm$^3$/h] | 590 | 8545 |
| CO [Nm$^3$/h] | 1 | 1907 |
| H2O [Nm$^3$/h] | 8046 | 5022 |
| Total flow [Nm$^3$/h] | 11461 | 16391 |
| $\Delta T_{app, SMR}$ [° C.] | | 10 |
| Power [kW] | 9899 | |
| Heat flux [kW/m$^2$] | 2.2 | |

Example 2

An example calculation of the process of the invention is given in Table 2 below. A hydrocarbon feed stream comprising i.a. a hydrocarbon gas, hydrogen and steam is fed to the reactor system of the invention. The feed stream entering the reactor system is pressurized to a pressure of 28 kg/cm$^2$·g and has a temperature of 500° C. Inside the reactor system, a structured catalyst in the form of 1 macroscopic structure having a square cross section is placed which has a size of 0.4 times 0.4 times 0.35 meter. The structured catalyst additionally has 10000 channels with a square cross section having a side or edge length of 0.32 cm. The structured catalyst has slits parallel to the longitudinal direction thereof, so that clusters of 5 times 5 channels are formed. The clusters are individually insulated from the neighboring cluster, except from the ends, so that the current path through the structured catalyst is a zigzag path. A current of 200 A and a voltage of ca. 500 V are applied to the structured catalyst of the reactor system of the invention in order to heat the structured catalyst and thus the gas passing over the structured catalyst, corresponding to a power deposited in the structured catalyst of 99 kW.

The reactor system in the current configuration could have an overall internal diameter of the reactor system of 1.2 m and a total internal height of 1.5 m when the reactor system is made as a cylindrical reactor system with spherical heads. In this specific configuration, the structured catalyst has a diagonal length of 0.6 m. Inert material is placed around the structured catalysts to close the gap to the insulation material which has an internal diameter of 0.6 m and a thickness of 0.3 m.

During the passage of the feed gas through the reactor system, the feed gas is heated by the structured catalyst and undergoes steam reforming to a product gas having an exit temperature of 963° C.

TABLE 2

Size of structured catalyst:

| | |
|---|---|
| Edge size [m] | 0.4 |
| Height [m] | 0.35 |
| Number of macroscopic structures | 1 |
| Total volume [L] | 55.4 |

| | Feed gas | Product gas |
|---|---|---|
| T [° C.] | 500 | 963 |
| P [kg/cm$^2$ g] | 27.97 | 27.47 |
| CO2 [Nm$^3$/h] | 1.7 | 7.3 |
| N2 [Nm$^3$/h] | 0.3 | 0.3 |
| CH4 [Nm$^3$/h] | 26.3 | 1.6 |
| H2 [Nm$^3$/h] | 5.9 | 85.4 |
| CO [Nm$^3$/h] | 0 | 19.1 |
| H2O [Nm$^3$/h] | 80.5 | 50.2 |
| Total flow [Nm$^3$/h] | 114.7 | 163.9 |
| $\Delta T_{app, SMR}$ [° C.] | | 10 |
| Power [kW] | 99 | |
| Heat flux [kW/m$^2$] | 2.2 | |

Example 3

An example calculation of the process of the invention is given in Table 3 below. A hydrocarbon feed stream comprising i.a. a hydrocarbon gas, hydrogen and steam is fed to the reactor system of the invention. The feed stream entering the reactor system is pressurized to a pressure of 97 bar, viz. 97 kg/cm$^2$·g and has a temperature of 500° C.

Inside the reactor system, a structured catalyst comprising nine macroscopic structures having a square cross section are placed in an array and each macroscopic structure has a size of 0.53 times 0.53 times 2.3 meter. Each macroscopic structure additionally has 17778 channels with a square cross section having a side or edge length of 0.32 cm. Each macroscopic structure has slits parallel to the longitudinal direction thereof, so that clusters of 5 times 5 channels are formed. The clusters are individually insulated from the neighboring cluster, except from the ends so that the current path through the structured catalyst is a zigzag path. A current of 200 A and a voltage of ca. 5.5 kV are applied to each macroscopic structure in the reactor system of the invention in order to heat the structured catalyst and thus the gas passing over the structured catalyst, corresponding to a power deposited in the structured catalyst of 9899 kW.

The reactor system in the current configuration could have an overall internal diameter of the reactor system of 3.2 m and a total internal height of 5.5 m when the reactor system is made as a cylindrical reactor system with spherical heads. In this specific configuration, the structured catalysts are placed in a square orientation having a diagonal length of 2.3 m. Inert material is placed around the structured catalysts to close the gap to the insulation material which has an internal diameter of 2.5 m and a thickness of 0.35 m.

During the passage of the feed gas through the reactor system, the feed gas is heated by the structured catalyst and undergoes steam reforming to a product gas having an exit temperature of 1115° C. It is seen from Table 3 that the total flows of the feed gas and the product gas are lower in Example 3 compared to Example 1.

Since the product gas exiting the reactor system is pressurized to a pressure of 97 bar, no compressors will be needed downstream the reactor system when a high pressure product gas is requested. This reduces the overall cost of a plant with a reactor system of the invention.

TABLE 3

Size of structured catalyst:

| | |
|---|---|
| Edge size [m] | 0.53 |
| Height [m] | 2.3 |
| Number of macroscopic structures | 9 |
| Total volume [L] | 5888 |

| | Feed gas | Product gas |
|---|---|---|
| T [° C.] | 500 | 1115 |
| P [kg/cm² g] | 96.97 | 96.47 |
| CO2 [Nm³/h] | 111 | 510 |
| N2 [Nm³/h] | 23 | 23 |
| CH4 [Nm³/h] | 2337 | 143 |
| H2 [Nm³/h] | 372 | 7354 |
| CO [Nm³/h] | 1 | 1796 |
| H2O [Nm³/h] | 7111 | 4518 |
| Total flow [Nm³/h] | 9955 | 14344 |
| $\Delta T_{app,\ SMR}$ [° C.] | | 10 |
| Power [kW] | 9899 | |
| Heat flux [kW/m²] | 2.2 | |

Example 4

An example calculation of the process of the invention is given in Table 3 below. A hydrocarbon feed stream comprising i.a. a hydrocarbon gas, hydrogen and steam is fed to the reactor system of the invention. The feed stream entering the reactor system is pressurized to a pressure of 28 bar, viz. 28 kg/cm²·g and has a temperature of 500° C.

Inside the reactor system, structured catalyst comprising 25 macroscopic structures having a square cross section are placed in an array and each macroscopic structure has a size of 0.24 times 0.24 times 1.8 meter. Each macroscopic structure additionally has 4702 channels with a square cross section having a side or edge length of 0.33 cm in length. Each macroscopic structure has slits parallel to the longitudinal direction thereof, so that clusters of 10 times 10 channels are formed. The clusters are individually insulated from the neighboring cluster, except from the ends, so that the current path through the structured catalyst is a zigzag path. A current of 500 A and a voltage of ca. 792 V are applied to each macroscopic structure in the reactor system of the invention in order to heat the structured catalyst and thus the gas passing over the structured catalyst, corresponding to a power deposited in the structured catalyst of 9899 kW.

The reactor system in the current configuration could have an overall internal diameter of the reactor system of 2.3 m and a total internal height of 4.1 m when the reactor system is made as a cylindrical reactor system with spherical heads. In this specific configuration, the structured catalysts are placed in a square orientation having a diagonal length of 1.7 m. Inert material is placed around the structured catalysts to close the gap to the insulation material which has an internal diameter of 1.8 m and a thickness of 0.25 m.

During the passage of the feed gas through the reactor system, the feed gas is heated by the structured catalyst and undergoes steam reforming to a product gas having an exit temperature of 963° C. It is seen from Table 4 that the structured catalyst of Example 4 is somewhat smaller than the one used in Examples 1 and 3 due to the higher current. The total flows of the feed gas and the product gas correspond to the flows of Example 1.

TABLE 4

Size of structured catalyst size:

| | |
|---|---|
| Edge size [m] | 0.24 |
| Height [m] | 1.8 |
| Number of macroscopic structures | 25 |
| Total volume [L] | 2562 |

| | Feed gas | Product gas |
|---|---|---|
| T [° C.] | 500 | 963 |
| P [kg/cm² g] | 27.97 | 27.47 |
| CO2 [Nm³/h] | 168 | 727 |
| N2 [Nm³/h] | 26 | 26 |
| CH4 [Nm³/h] | 2630 | 164 |
| H2 [Nm³/h] | 590 | 8545 |
| CO [Nm³/h] | 1 | 1907 |
| H2O [Nm³/h] | 8046 | 5022 |
| Total flow [Nm³/h] | 11461 | 16391 |
| $\Delta T_{app,\ SMR}$ [° C.] | | 10 |
| Power [kW] | 9899 | |
| Heat flux [kW/m²] | 3.6 | |

Example 5

An example calculation of the process of the invention is given in Table 4 below. A hydrocarbon feed stream comprising i.a. a hydrocarbon gas, hydrogen and steam is fed to the reactor system of the invention. The feed stream entering the reactor system is pressurized to a pressure of 182 bar and has a temperature of 500° C.

Inside the reactor system, a structured catalyst comprising nine macroscopic structures having a square cross section are placed in an array and each macroscopic structure has a size of 0.53 times 0.53 times 2.3 meter. Each macroscopic structure additionally has 17778 channels with a square cross section having a side or edge length of 0.32 cm. Each macroscopic structure has slits parallel to the longitudinal direction thereof, so that clusters of 5 times 5 channels are formed. The clusters are individually insulated from the neighboring cluster, except from the ends, so that the current path through the structured catalyst has a zigzag path. A current of 200 A and a voltage of ca. 5.5 kV are applied to each macroscopic structure in the reactor system of the invention in order to heat the structured catalyst and thus the gas passing over the structured catalyst, corresponding to a power deposited in the structured catalyst of 9899 kW.

The reactor system in the current configuration could have an overall internal diameter of the reactor system of 3.2 m and a total internal height of 5.5 m when the reactor system is made as a cylindrical reactor system with spherical heads. In this specific configuration, the structured catalysts are placed in a square orientation having a diagonal length of 2.3 m. Inert material is placed around the structured catalysts to close the gap to the insulation material which has an internal diameter of 2.5 m and a thickness of 0.35 m.

During the passage of the feed gas through the reactor system, the feed gas is heated by the structured catalyst and undergoes steam reforming to a product gas having an exit temperature of 1236° C. The total flows of the feed gas and the product gas are lower than the total flows of the gasses in Examples 1 and 4.

Since the product gas exiting the reactor system is already pressurized to a pressure of 181 bar, it is suited for being input into an ammonia plant without further pressurizing. Thus, no compressors will be needed between the reactor system and the ammonia loop of the ammonia plant. This reduces the overall cost of the plant with a reactor system of the invention and an ammonia loop.

TABLE 5

Size of structured catalyst size:

| | |
|---|---|
| Edge size [m] | 0.53 |
| Height [m] | 2.3 |
| Number of macroscopic structures | 9 |
| Total volume [L] | 5888 |

| | Feed gas | Product gas |
|---|---|---|
| T [° C.] | 500 | 1236 |
| P [kg/cm² g] | 181.97 | 181 |
| CO2 [Nm³/h] | 86 | 395 |
| N2 [Nm³/h] | 21 | 21 |
| CH4 [Nm³/h] | 2116 | 96 |
| H2 [Nm³/h] | 278 | 6648 |
| CO [Nm³/h] | 0 | 1711 |
| H2O [Nm³/h] | 6425 | 4096 |
| Total flow [Nm³/h] | 8926 | 12967 |
| $\Delta T_{app,\,SMR}$ [° C.] | | 10 |
| Power [kW] | 9899 | |
| Heat flux [kW/m²] | 2.2 | |

Example 6

Example 6 relates to a reactor system comprising a structured catalyst in the form of a macroscopic structure having in total 78540 channels with a total wall length of one channel in the cross section of 0.00628 m each and a length of 2 m, giving a total surface area of 987 m² of catalyst surface. For a reactor system with this structured catalyst, a simulation with varying gas flow over the structured catalyst was made where the gas composition in all calculations was 8.8% $H_2$, 56.8% $H_2O$, 0.2% $N_2$, 0.1% CO, 2.3% $CO_2$, and 31.8% $CH_4$. In each simulation a kinetic model for steam reforming and water gas shift was used and a variation in the surface flux (Q) of energy from the electrically heated structured catalyst was made to adjust the exit temperature of the product gas from the reactor system housing the structured catalyst to 920° C. The kinetic model used was similar to the approach used by Xu and Froment, (J. Xu and G. F. Froment, Methane steam reforming, methanation and water-gas shift: I. intrinsic kinetics. American Institution of Chemical Engineers Journal, 35:88-96, 1989.). FIG. 11 shows the approach to equilibrium along the reactor system length at varying total flows. The Figure shows that at low feed flows (10000 Nm³/h), the approach to the equilibrium at the outlet the reactor system is below 5° C., which translate into a hydrocarbon conversion of 77%, while at the high flows (150000 Nm³/h) the approach to equilibrium is above 60° C., which correspond to a hydrocarbon conversion of only 64%, and the hydrocarbons therefore are used less efficiently. The close control of the heat flux in the current invention therefore allows for controlling the approach to equilibrium closely along the length of the reactor system. A general trend in all the curves in FIG. 11 is that the approach to equilibrium is continuously decreasing until a pseudo equilibrium is reached, where the heat added and the heat consumed roughly equal each other. The approach to equilibrium from this stage is substantially constant or has a slightly increasing development due to the overall increasing temperature of the reactor system.

Example 7

An example calculation of a process of the invention is given in Table 6 below. A hydrocarbon feed stream comprising i.a. a hydrocarbon gas and hydrogen is fed to the reactor system of the invention. The feed stream entering the reactor system is pressurized to a pressure of 3.2 bar, viz. 3.2 kg/cm²·g, and has a temperature of 500° C.

Inside the reactor system, a structured catalyst comprising 25 macroscopic structures having a square cross section are placed in an array, where each macroscopic structure has a size of 0.24 times 0.24 times 1.8 meter. Each macroscopic structure additionally has 4702 channels with a square cross section having a side or edge length of 0.33 cm in length. Each macroscopic structure has slits parallel to the longitudinal direction thereof, so that clusters of 10 times 10 channels are formed. The clusters are individually insulated from the neighboring cluster, except from the ends, so that the current path through the structured catalyst is a zigzag path. A current of 500 A and a voltage of ca. 787 V are applied to each macroscopic structure in the reactor system of the invention in order to heat the structured catalyst and thus the gas passing over the structured catalyst, corresponding to a power deposited in the structured catalyst of 9858 kW.

The reactor system in the current configuration has an overall internal diameter of the reactor system of 2.3 m and a total internal height of 4.1 m when the reactor system is made as a cylindrical reactor system with spherical heads. In this specific configuration, the structured catalyst is placed in a square orientation having a diagonal length of 1.7 m. Inert material is placed around the structured catalyst to close the gap to the insulation material which has an internal diameter of 1.8 m and a thickness of 0.25 m.

During the passage of the feed gas through the reactor system, the feed gas is heated by the structured catalyst and undergoes propane dehydrogenation and thermal cracking to a product gas having an exit temperature of 600° C.

TABLE 6

Size of structured catalyst:

| | |
|---|---|
| Edge size [m] | 0.24 |
| Height [m] | 1.8 |
| Number of macroscopic structures | 25 |
| Total volume [L] | 2562 |

| | Feed gas | Product gas |
|---|---|---|
| T [° C.] | 500 | 600 |
| P [kg/cm² g] | 3.24 | 2.73 |
| $C_3H_8$ [Nm³/h] | 18918 | 14747 |
| $N_2$ [Nm³/h] | 0.0 | 0.0 |
| $H_2$ [Nm³/h] | 9450 | 12739 |
| $C_3H_6$ [Nm³/h] | 0 | 3721 |
| $CH_4$ [Nm³/h] | 43 | 487 |
| $C_2H_6$ [Nm³/h] | 1338 | 1767 |
| $C_2H_4$ [Nm³/h] | 19 | 33 |
| Total flow [Nm³/h] | 29770 | 33495.8 |
| $\Delta T_{app,\,PDH}$ [° C.] | | |
| Power [kW] | 9858 | |
| Heat flux [kW/m²] | 3.59 | |

The invention claimed is:

1. A reactor system for carrying out an endothermic reaction of a feed gas, said reactor system comprising:
   a structured catalyst arranged for catalyzing said endothermic reaction of said feed gas, said structured catalyst comprising a macroscopic structure of electrically conductive material, said macroscopic structure supporting a ceramic coating, wherein said ceramic coating supports a catalytically active material;
   a pressure shell housing said structured catalyst;
   a heat insulation layer between said structured catalyst and said pressure shell; and at least two conductors electrically connected to said structured catalyst and to an electrical power supply placed outside said pressure shell, wherein said electrical power supply is dimensioned to heat at least part of said structured catalyst to a temperature of at least 200° C. by passing an electrical current through said electrically conductive material, wherein the pressure shell comprises an inlet at a first end of the pressure shell for letting in process gas and an outlet at a second end of the pressure shell for letting out product gas, and wherein the at least two conductors are connected to the structured catalyst at a position closer to the inlet than to the outlet.

2. The reactor system according to claim 1, wherein the pressure shell has a design pressure of between 2 and 30 bar.

3. The reactor system according to claim 1, wherein the pressure shell has a design pressure of between 30 and 200 bar.

4. The reactor system according to claim 1, wherein the resistivity of the electrically conductive material is between $10^{-5}$ Ω·m and $10^{-7}$ Ω·m.

5. The reactor system according to claim 1, where said at least two conductors are led through the pressure shell in a fitting so that the at least two conductors are electrically insulated from the pressure shell.

6. The reactor system according to claim 5, wherein said pressure shell further comprises one or more inlets, including the inlet, close to or in combination with at least one fitting in order to allow a cooling gas to flow over, around, close to, or inside at least one conductor within said pressure shell.

7. The reactor system according to claim 1, wherein the reactor system further comprises an inner tube in heat exchange relationship with but electrically insulated from the structured catalyst, said inner tube being adapted to withdraw the product gas from the structured catalyst so that the product gas flowing through the inner tube is in heat exchange relationship with gas flowing over the structured catalyst.

8. The reactor system according to claim 1, wherein the connection between the structured catalyst and said at least two conductors is a mechanical connection, a welded connection, a brazed connection or a combination thereof.

9. The reactor system according to claim 1, wherein the electrically conductive material comprises an 3D printed or extruded and sintered macroscopic structure, said macroscopic structure is supporting a ceramic coating, wherein said ceramic coating supports a catalytically active material.

10. The reactor system according to claim 9, wherein said macroscopic structure has a plurality of parallel channels, a plurality of non-parallel channels and/or a plurality of labyrinthic channels.

11. The reactor system according to claim 10, wherein said reactor system further comprises a third catalyst material in the form of catalyst pellets, extrudates or granulates loaded into the channels of said macroscopic structure.

12. The reactor system according to claim 1, wherein the structured catalyst comprises an array of macroscopic structures electrically connected to each other.

13. The reactor system according to claim 1, wherein the reactor system further comprises a bed of a second catalyst material upstream said structured catalyst within said pressure shell.

14. The reactor system according to claim 1, wherein said reactor system further comprises a control system arranged to control the electrical power supply to ensure that the temperature of the gas exiting the pressure shell lies in a predetermined range and/or to ensure that the conversion of the feed gas lies in a predetermined range.

15. The reactor system according to claim 1, wherein the structured catalyst within said reactor system has a ratio between the area equivalent diameter of a horizontal cross section through the structured catalyst and the height of the structured catalyst in the range from 0.1 to 2.0.

16. The reactor system according to claim 1, wherein the height of the reactor system is between 0.5 and 7 m.

17. The reactor system according to claim 16, wherein the height of the reactor system is between 0.5 and 3 m.

18. The reactor system according to claim 1, further comprising electrically insulating parts provided in the structured catalyst and positioned between the at least two conductors.

* * * * *